(12) United States Patent
De Lange et al.

(10) Patent No.: US 8,563,279 B2
(45) Date of Patent: Oct. 22, 2013

(54) CONVERGENT SYNTHESIS OF RENIN INHIBITORS AND INTERMEDIATES USEFUL THEREIN

(75) Inventors: Ben De Lange, Munstergeleen (NL); Anna Maria Cornelia Francisca Castelijns, Spaubeek (NL); Johannes Gerardus De Vries, Maastricht (NL); Andreas Hendrikus Maria De Vries, Maastricht (NL); Jeroen Antonius Franciscus Boogers, Maastricht (NL); Quirinus Bernardus Broxterman, Munstergeleen (NL)

(73) Assignee: DSM IP Assets B.V., Heerlen (NL)

( * ) Notice: Subject to any disclaimer, the term of this patent is extended or adjusted under 35 U.S.C. 154(b) by 383 days.

(21) Appl. No.: 12/810,220

(22) PCT Filed: Dec. 19, 2008

(86) PCT No.: PCT/EP2008/068072
§ 371 (c)(1),
(2), (4) Date: Sep. 22, 2010

(87) PCT Pub. No.: WO2009/080773
PCT Pub. Date: Jul. 2, 2009

(65) Prior Publication Data
US 2011/0008852 A1    Jan. 13, 2011

(30) Foreign Application Priority Data
Dec. 24, 2007  (EP) .................................. 07025093

(51) Int. Cl.
| | |
|---|---|
| *C07C 231/18* | (2006.01) |
| *C07C 253/16* | (2006.01) |
| *C07C 255/20* | (2006.01) |
| *C07F 1/02* | (2006.01) |
| *C07F 7/18* | (2006.01) |
| *C07D 307/32* | (2006.01) |
| *C07D 307/33* | (2006.01) |
| *C12P 13/00* | (2006.01) |

(52) U.S. Cl.
USPC ........... 435/128; 549/321; 556/173; 556/402; 556/438; 558/348; 558/441; 568/613

(58) Field of Classification Search
None
See application file for complete search history.

(56) References Cited

U.S. PATENT DOCUMENTS 7,009,078 B1 * 3/2006 Herold et al. ................. 564/161

FOREIGN PATENT DOCUMENTS

| WO | WO 03/047576 | 6/2003 |
| WO | WO 2006/061427 | 6/2006 |
| WO | WO 2006/131304 | 12/2006 |
| WO | WO 2007/009250 | 1/2007 |

OTHER PUBLICATIONS

Ravenna et al., caplus an 1930:37267.*
Ravenna et al., caplus an 1930:37267 , 1930.*
International Search Report for PCT/EP2008/068072, mailed Apr. 7, 2009.
Written Opinion for PCT/EP2008/068072, mailed Apr. 7, 2009.
Sandham et al., "A convergent synthesis of the renin inhibitor CGP60536B", *Tetrahedron Letters*, vol. 41, No. 51, Dec. 2000, pp. 10091-10094, XP004225223.
Dondoni et al., "A convergent synthesis of the renin inhibitor SPP-100 using a nitrone intermediate", *Tetrahedron Letters*, nol. 42, No. 29 Jul. 2001, pp. 4819-4823, XP004247360.
Lindsay et al., "Formal total synthesis of the potent renin inhibitor aliskiren: Application of a SmI2-promoted acyl-like radical coupling", *Journal of Organic Chemistry*, vol. 71, No. 13, May 2006, pp. 4766-4777, XP002405545.

* cited by examiner

*Primary Examiner* — Sun Jae Loewe
(74) *Attorney, Agent, or Firm* — Nixon & Vanderhye P.C.

(57) ABSTRACT

Described is a method for the preparation of renin inhibitors such as aliskiren, and intermediates useful therein. The method introduces a nitrogen-containing intermediate such as a lactone of formula (8). with $R_4$ being a branched $C_{3-6}$ alkyl. In the preparation of the lactone, or related intermediates, a desired stereochemical configuration can be controlled by starting from a chiral aldehyde satisfying formula (10).

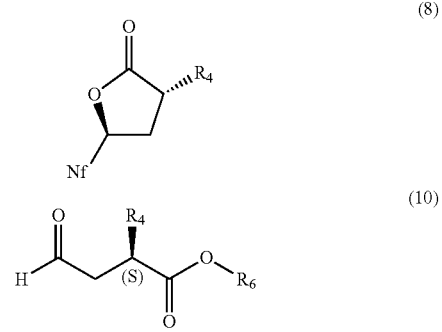

12 Claims, No Drawings

CONVERGENT SYNTHESIS OF RENIN INHIBITORS AND INTERMEDIATES USEFUL THEREIN

This application is the U.S. national phase of International Application No. PCT/EP2008/068072 filed 19 Dec. 2008 which designated the U.S. and claims priority to EP Patent Application No. 07025093.1 filed 24 Dec. 2007, the entire contents of each of which are hereby incorporated by reference.

The invention pertains to a convergent synthesis route for the preparation of certain 2(S),4(S),5(S),7(S)-2,7-dialkyl-4-hydroxy-5-amino-8-aryl-octanoyl amide derivatives, or pharmaceutically acceptable salts thereof, such as the compound aliskiren. The invention particularly relates to a synthetic route that will introduce the nitrogen of the above mentioned compounds ultimately required for the amino-group at C-5, at a relative early stage of the synthesis. The invention further relates to novel intermediates useful in the manufacture of the above mentioned compounds. Particularly, the 2(S),4(S),5(S),7(S)-2,7-dialkyl-4-hydroxy-5-amino-8-aryl-octanoyl amide derivatives to which the methods of the present invention applies are any of those having renin inhibitory activity and, therefore, pharmaceutical utility, e.g., those disclosed in U.S. Pat. No. 5,559,111, WO 2006/061427, or WO 2006/095020.

The 2(S),4(S),5(S);7(S)-2,7-dialkyl-4-hydroxy-5-amino-8-aryl-octanoyl amide derivatives, or pharmaceutically acceptable salts thereof to which the invention pertains, satisfy the general formula (1).

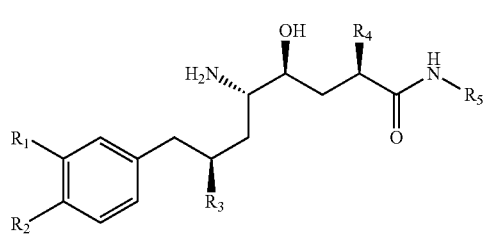

Herein $R_1$ is halogen, $C_{1-6}$halogenalkyl, $C_{1-6}$alkoxy-$C_{1-6}$alkoxy or $C_{1-6}$alkoxy-$C_{1-6}$alkyl; $R_2$ is halogen, $C_{1-6}$alkyl or $C_{1-6}$alkoxy; $R_3$ and $R_4$ are independently branched $C_{3-6}$alkyl; and $R_5$ is $C_{1-12}$cycloalkyl, $C_{1-12}$alkyl, $C_{1-12}$hydroxyalkyl, $C_{1-6}$alkoxy-$C_{1-6}$alkyl, $C_{1-6}$alkanoyloxy-$C_{1-6}$alkyl, $C_{1-12}$aminoalkyl, $C_{1-6}$alkylamino-$C_{1-6}$alkyl, $C_{1-6}$dialkylamino-$C_{1-6}$alkyl, $C_{1-6}$alkanoylamino-$C_{1-6}$alkyl, HO—(O)C—$C_{1-12}$alkyl, $C_{1-6}$alkyl-O—(O)C—$C_{1-6}$alkyl, $H_2N$—C(O)—$C_{1-12}$alkyl, $C_{1-6}$alkyl-HN—C(O)—$C_{1-6}$alkyl, $(C_{1-6}$alkyl$)_2$-N—C(O)—$C_{1-6}$alkyl; saturated, unsaturated, or partially saturated $C_{1-12}$heterocyclyl bonded via a carbon atom, and which heterocyclyl is optionally substituted one or more times by $C_{1-6}$alkyl, trifluoromethyl, nitro, amino, N-mono- or N,N-di-$C_{1-6}$alkylated amino, $C_{1-6}$alkanoyl, $C_{2-6}$alkenyl, $C_{2-6}$alkynyl, $C_{1-6}$alkoxy, $C_{1-6}$alkoxycarbonylamino, $C_{0-6}$alkylcarbonylamino, $C_{1-6}$alkylcarbonyloxy, $C_{1-12}$aryl, N-mono or N,N-di-$C_{1-6}$alkylated carbamoyl, optionally esterified carboxyl, cyano, halogen, halo-$C_{1-6}$alkoxy, halo-$C_{1-6}$alkyl, $C_{1-12}$heteroaryl, saturated, unsaturated or partially saturated $C_{1-6}$heterocyclyl, hydroxyl, nitro; or the salt of compound according to formula (1), especially pharmaceutically acceptable salt thereof.

In the convergent synthesis of compounds according to formula (1), it is known to separately provide e.g. two synthons commensurate with the following structural parts and, in the course of the entire synthesis route, couple these and convert as necessary. A reference in this respect is Sandham et al. Tetrahedron Letters 2000, 41, 10091-10094.

The structural parts referred to are an aromatic part typically satisfying the structural formula (5),

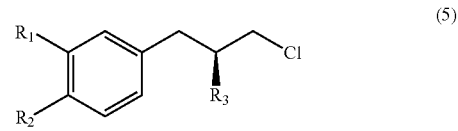

wherein $R_1$ is 3-methoxy-propoxy, $R_2$ is methoxy, and $R_3$ are 2-propyl, and the Cl-group is transferred to the corresponding Grignard compound and subsequently transmetallated with $CeCl_3$, prior to the coupling with an aldehyde part typically satisfying the structural formula (3),

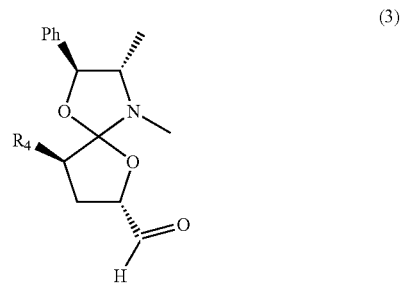

wherein $R_4$, is 2-propyl, and Ph stands for phenyl.

The above more particularly pertains to the synthesis of compounds of formula (4), the fumaric acid salt of which is known as aliskiren, (2S,4S,5S,7S)-7-(3-(3-methoxypropoxy)-4-methoxybenzyl)-5-amino-N-(2-carbamoyl-2-methylpropyl)-4-hydroxy-2-isopropyl-8-methylnonanamide.

In the present application, any reference to aliskiren is deemed to include reference to all pharmaceutically acceptable salts, and prodrugs thereof.

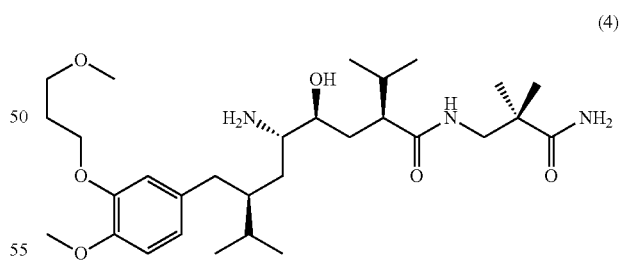

For the synthesis of the aforementioned parts, and the resulting linked compounds, generally multistep processes are used. In typical cases, the yields of one or more of these steps are low, and the overall yield is further affected by the desire to ultimately obtain a diastereomerically pure compound.

A critical step in the process is the chemo- and stereoselective introduction of nitrogen so as to create the 5-amino group. In the above routes of synthesis, the nitrogen is introduced after coupling of the described structural parts by substituting the obtained alcohol moiety using several, laborious steps. Moreover, some of these steps are difficult to perform at production scale.

Coupling of the compound of formula (5) wherein $R_1$ is 3-methoxy-propoxy, $R_2$ is methoxy, and $R_3$ are 2-propyl, with a nitrogen containing building block derived from the compound of formula (3) is Dondoni et al. Tetrahedron Letters 2001, 41, 4819-4823, wherein, prior to the coupling, the Cl-group of compound according to formula (5) is transferred to the corresponding Grignard compound and subsequently transmetallated with $CeCl_3$.

This route results, at best, in a very small excess of the desired diastereomer (55:45), only if additional measures are employed, such as the addition of a chelate complex-destroying agent. In general, the opposite of the desired diastereomer is obtained in excess. As indicated in the paper, a substantial dominance of the desired S-epimer could not be achieved.

The invention now provides a novel route for coupling new nitrogen containing compounds of formula (7) and (8) to a compound of formula (2) (see below). Surprisingly, such coupling can be achieved with a much simpler nitrogen containing compound, in particular a compound not comprising a chiral auxiliary. It is an advantage of the new nitrogen containing compounds, that the desired coupling products can be obtained with a higher yield of the compound with the desired configuration at the C-5 stereogenic center.

It would be advantageous to provide a convergent synthesis route for compounds of formula (1) which satisfies one or more of the following:
- a reduced number of steps;
- an improved overall yield;
- a relatively easy introduction of the "5-amino" group;
- providing a nitrogen-containing compound (preferably in a short and scalable route) that is capable of being coupled with the compound according to formula (2).

By preference, it would be advantageous to achieve one or more of the following:
- an increased diastereomeric selectivity in the aforementioned coupling step;
- providing an enantiomerically enriched (most preferably pure) nitrogen-containing compound that is capable of being coupled with the compound according to formula (2), resulting in the coupling product with the desired stereochemical configuration, or at least so as to provide the 5(S) configuration in excess.

In order to better address the foregoing, in one aspect, the invention provides a synthesis route to compounds of formula (1a).

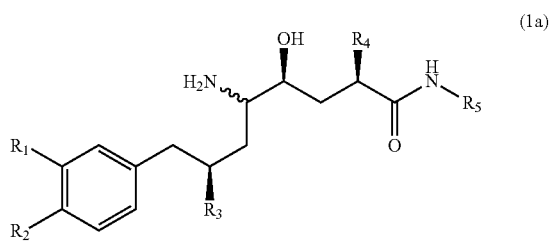

Herein, the R groups have the above-indicated meaning. The synthesis route is based on a novel nitrogen-containing compound according to formula (7), or the corresponding lactone of formula (8), as described below.

In another aspect, the invention provides a novel chiral aldehyde (10), as a precursor for the nitrogen-containing intermediates, and thus as an intermediate to facilitate the synthesis of the compounds concerned. In another aspect, the invention presents processes for the stereoselective conversion of the chiral aldehyde into the nitrogen containing compound.

In yet a further aspect, the invention provides the coupling of compounds of structure (2) with the nitrogen containing compounds of formula (7) and/or (8), under the appropriate conditions, resulting in compounds depicted by formula (9a) and/or (11a), with the configuration of the C-5 stereogenic center being undefined, optionally followed by a purifying step in order to obtain the desired configurational purity at the C-5 stereogenic center, or the coupling of compounds of structure (2) with the nitrogen containing compound of formula (7) and/or (8) is resulting in the compounds depicted by formula (9) and/or (11).

In a still further aspect, the invention provides a synthesis route to compounds of formula (1), notably to aliskiren and closely related compounds.

The overall synthetic route to compound (1), as an example of synthetic routes according to the invention, can be as follows:

Scheme I

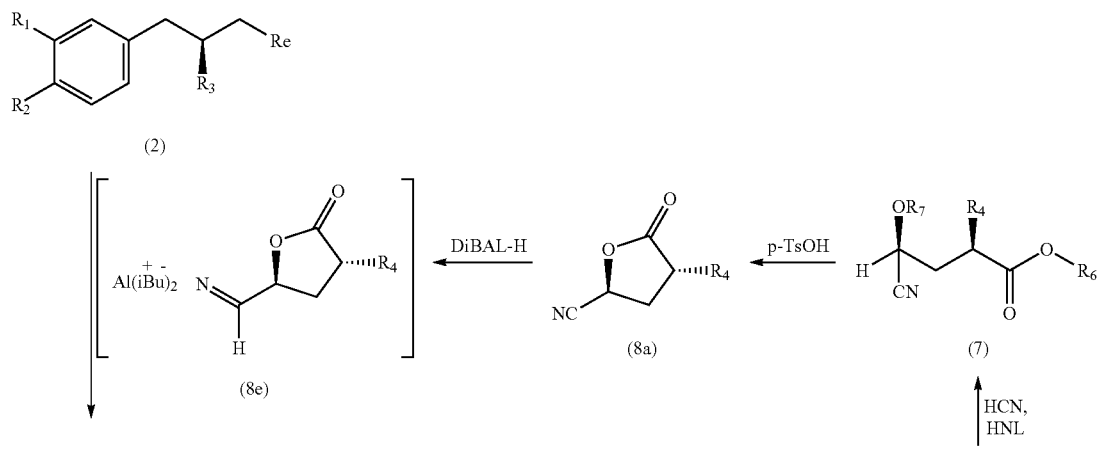

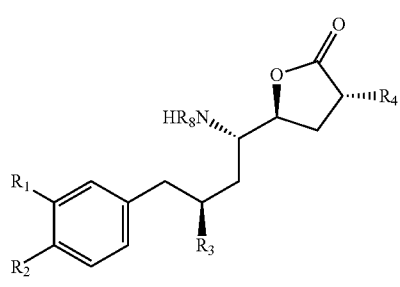

(11)

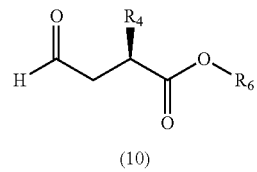

(10)

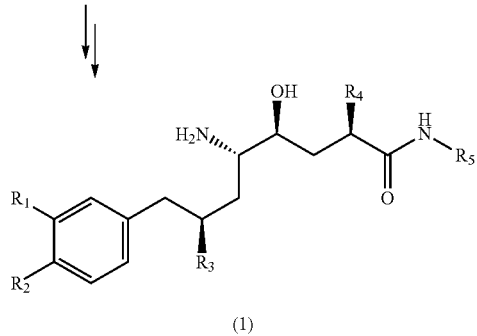

(1)

The abbreviations in this scheme, other than chemical elements have the following meaning:

DiBAL-H is diisobutyl aluminum hydride;
p-TsOH is para-toluene sulfonic acid;
HNL is hydroxynitrile lyase;
$R_1$, $R_2$, $R_3$, $R_4$, and $R_5$ are as described for the compound according to formula (1);
Re is a reactive moiety selected from F; Cl; Br; I; $M(X)_n$, wherein X is F, Cl, Br, I, CN, $C_{1-12}$alkyl, or $C_{1-6}$alkoxy and M is a metal, preferably M is Mg, Ce, Li, Ba, Al, B, Cu, Zn, Mn, Ti, Zr, In and n is 0, 1, 2, 3, or 4; $MM'(X)_n$ $(Y)_{n'}$, wherein M and M' are a metal, preferably M and M' are each independently Mg, Ce, Li, Ba, Al, B, Cu, Zn, Mn, Ti, Zr, In, where X and Y are each independently chosen from F, Cl, Br, I, or CN, $C_{1-12}$alkyl, $C_{1-6}$alkoxy and n, n' are each independently chosen from the values as described above; or Re is $OR_9$, wherein $R_9$ is a group capable of making $OR_9$ a leaving group, such group being known to the person skilled in the art, for example $R_9$ is acetyl, trifluoroacetyl; $CF_3SO_2$, $CH_3SO_2$, $CH_3C_6H_4SO_2$, $C(O)OCH_3$, or $C(O)OC_4H_9$;
$R_6$ represents H, or optionally substituted $C_{1-12}$alkyl, optionally substituted $C_{1-12}$alkylaryl, or optionally substituted $C_{1-12}$aryl;
$R_7$ represents H, or is an O-protecting group as described in J. F. W. McOmie, "Protective Groups in Organic Chemistry", Plenum Press, London and New York 1973; or in T. W. Greene and P. G. M. Wuts, "Protective Groups in Organic Synthesis", Third edition, Wiley, New York 1999;
or $R_6$ forms with $R_7$ an, optionally substituted $C_{1-12}$(hetero)cyclic compound, as such protecting both the acid and alcohol group;
$R_8$ denotes H, or a group remaining after the reaction of the Nf group as it was present in compound of formula (8), or $R_8$ represents a group, put on independently in an additional reaction step, making the moiety attached via the N-atom to the C-5 stereogenic center of the compound depicted by formula (11) inactive for reaction steps thereafter, With reference to the overall reaction Scheme I, the various novel intermediates and the various related reaction steps are separately discussed hereinafter.

The Nitrogen-Containing Compounds

This can be a compound depicted by formula (7), or the corresponding lactone compound of formula (8):

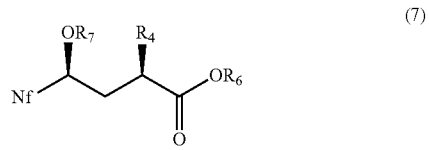

(7)

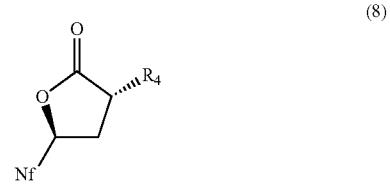

(8)

In these formulae, $R_4$ has the meaning given above with reference to formula (1). In the specific synthesis route to aliskiren, this represents a 2-propyl group.

$R_4$, $R_6$, and $R_7$, have the meaning given above, and Nf is a group comprising a carbon atom directly bonded to a nitrogen atom, preferably Nf is a group resulting in the compounds depicted by formulae (7a) to (7h), and compounds depicted by formulae (8a) to (8h),

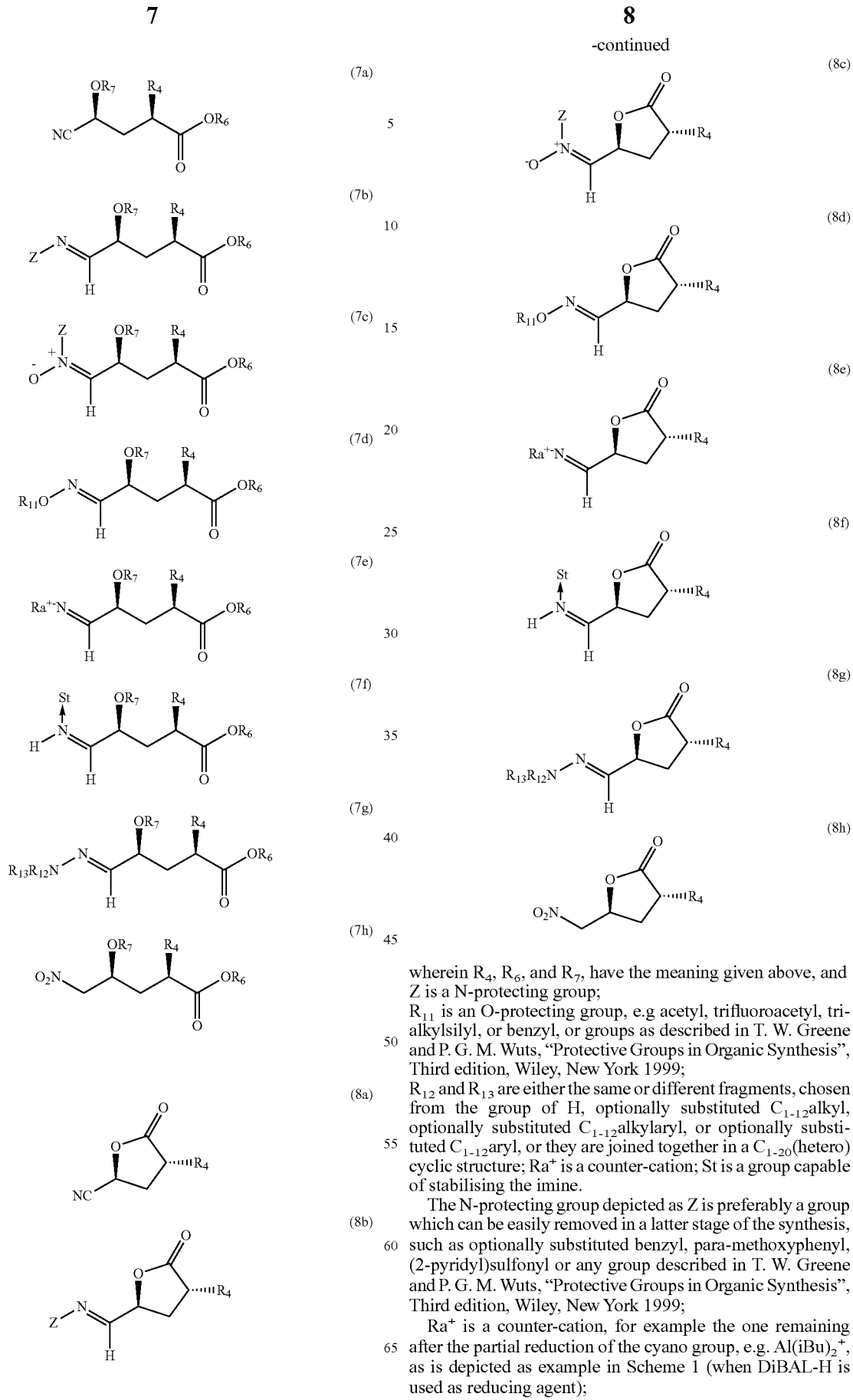

wherein $R_4$, $R_6$, and $R_7$, have the meaning given above, and Z is a N-protecting group;

$R_{11}$ is an O-protecting group, e.g acetyl, trifluoroacetyl, trialkylsilyl, or benzyl, or groups as described in T. W. Greene and P. G. M. Wuts, "Protective Groups in Organic Synthesis", Third edition, Wiley, New York 1999;

$R_{12}$ and $R_{13}$ are either the same or different fragments, chosen from the group of H, optionally substituted $C_{1-12}$alkyl, optionally substituted $C_{1-12}$alkylaryl, or optionally substituted $C_{1-12}$aryl, or they are joined together in a $C_{1-20}$(hetero)cyclic structure; $Ra^+$ is a counter-cation; St is a group capable of stabilising the imine.

The N-protecting group depicted as Z is preferably a group which can be easily removed in a latter stage of the synthesis, such as optionally substituted benzyl, para-methoxyphenyl, (2-pyridyl)sulfonyl or any group described in T. W. Greene and P. G. M. Wuts, "Protective Groups in Organic Synthesis", Third edition, Wiley, New York 1999;

$Ra^+$ is a counter-cation, for example the one remaining after the partial reduction of the cyano group, e.g. $Al(iBu)_2^+$, as is depicted as example in Scheme 1 (when DiBAL-H is used as reducing agent);

St is a group capable of stabilising the imine, preferably the remaining group after partial reduction of the cyano group, e.g. $B(R_{10})_3$, if $LiBH(R_{10})_3$ was used, $R_{10}$ being H or a $C_{1-6}$ alkyl group.

The partial reduction of the nitrile group in the compounds depicted by formulae (7a) and (8a), resulting in compounds of formula (7e and f) and (8e and f), can be conducted in a variety of ways known to the skilled person, as described in Andreoli et al. J. Org. Chem. 1990, 55, 4199-4200; Masahiko et al. Synlett 1991, 7, 479-480; Zandbergen et al. Tetrahedron 1992, 48, 3977-3982; Cainelli et al. Tetrahedron 1993, 49, 3809-3826; Itsuno et al. J. Chem. Soc. Perkin Trans. I 1991, 1767-1769; Ramachandran and Biaswas Org. Lett. 2007, 9, 3025-3027.

The cyanohydrin compound of formula (7a) (Nf=CN) can be prepared by reacting the chiral aldehyde of formula (10) with a cyanide, preferably with HCN, NaCN, KCN, $(R)_3SiCN$ (with R selected from $C_{1-6}$alkyl, $C_{1-10}$alkylaryl, and $C_{1-6}$aryl), optionally in the presence of a chiral catalyst. Said catalyst can be a chiral organic compound, a chiral metal complex, or an enzyme, as described in by F. X. Chen and X. M. Feng in "Asymmetric synthesis of cyanohydrins" Current Organic Synthesis 2006, 3, 77-97, and references therein; and by P. Poechlauer, W. Skranc, and M. Wubbolts in "The large-scale biocatalytic synthesis of enantiopure cyanohydrins" in Asymmetric Catalysis on Industrial Scale; H. U. Blaser and E. Schmidt, Eds. Wiley-VCH, 2004, pp 151-164. Preferably HCN, or $(R)_3SiCN$ in the presence of a suitable chiral catalyst is used. More preferred HCN and the enzyme HNL (hydroxynitrile lyase) are used. Suitable conditions for the synthesis of compound of formula (7a) are known by the person skilled in the art and are described in the references above, and references therein.

The nitrile containing compound of formula (7a) and (8a) can be converted to other nitrogen containing compounds according to formula (7b_g) and (8b-g) by using methods known in the art, for example by partial reduction as described above. Examples of various imine-type compounds, and applied conditions can be found in Bloch Chem. Rev. 1998, 98, 1407-1438; Friestad and Mathies Tetrahedron 2007, 63, 2541-2569 and references therein. Optionally, the partial reduction can be followed by immediate hydrolysis to the corresponding aldehyde group resulting in the formation of compounds of formula (6a) or (6b),

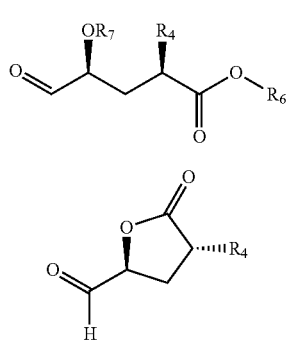

wherein $R_4$, $R_6$, and $R_7$, have the meaning given above, and subsequent reaction to the imine, oxime or hydrazone compounds. The compounds according to formula (6a) and (6b) can be purified and isolated, or immediately converted to the corresponding nitrogen containing compounds of formula (7) and (8). Preferably, the compounds according to formula (6a) and (6b) are converted without isolation to the corresponding nitrogen containing compounds of formula (7) and (8).

One example of such a preferred sequence (without isolation of compound of formula (6a) is depicted in Scheme II.

Scheme II

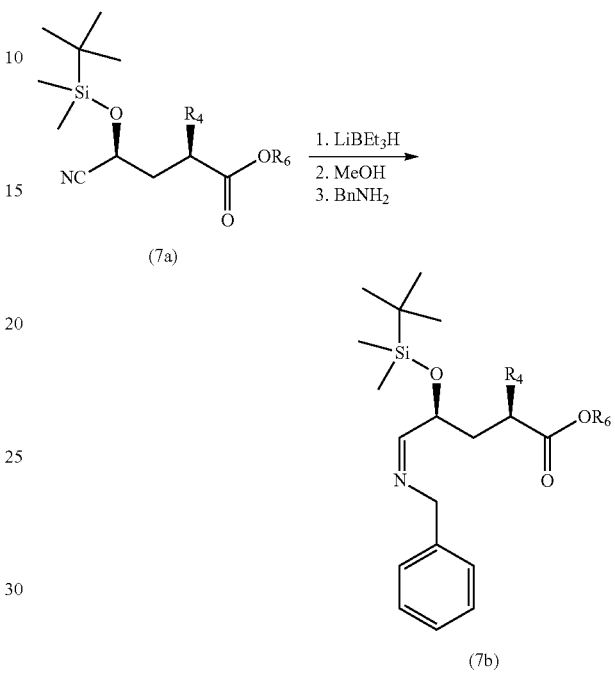

The nitro analogue of compound of formula (7h, Nf=(H)C(H)NO$_2$) can be prepared by addition of nitromethane to the chiral aldehyde of formula (10), the so-called Henry reaction, preferably in the presence of a chiral compound, said chiral compound can be an organic compound, a metal complex, or an enzyme. Preferably, said chiral compound is used in catalytic amounts, preferably less than 10 mol % compared to the amount of chiral aldehyde. Suitable examples of said chiral compounds are for example described by Boruwa et al. in Tetrahedron Asymmetry 2006, 17, 3315-3326 and references therein.

The nitrogen containing compounds of formula (7) can be converted into the corresponding lactone compounds of formula (8) by using methods known in the art, in analogy with regular deprotection methods and ester synthesis, e.g. catalyzed by para-toluene sulfonic acid. For the lacton formation, $R_6$ is preferentially $C_{1-6}$alkyl, more preferentially methyl.

The lactone nitrile of formula (8a) in the diastereochemically desired configuration can be obtained by ring-closing the cyanohydrin of formula (7a) in the desired configuration, or by ring-closing both diastereomers of the cyanohydrin of formula (7a) with fixed configuration at C-2 stereogenic center, followed by epimerization of the C-4 steroegenic center to the thermodynamically preferred diastereomer, also being the desired diastereomer. Said epimerisation can be conducted by heating the lactone nitrile, optionally in a suitable solvent, and optionally in the presence of a base or other suitable additives. Alternatively, the diastereoisomer with the desired configuration can be separated from the other diastereoisomer making use of their different physical properties (e.g. preferential crystallization), or by means of classic or separating moving beds (SMB) chromatography. Suitable examples of SMB chromatography can be found in Schulte and Strube J. Chromatogr. A 2001, 906, 399-416 and references therein.

Preferably the lactone nitrile of formula (8a) in the diastereochemically desired configuration is obtained by ring-closing an optically pure cyanohydrin of formula (7a).

It will be appreciated that the nitrogen-containing intermediates can be used in the synthesis of compounds of formula (1), as is depicted in the overall reaction scheme by reacting compound of formula (9a) or (11a), or a mixture thereof, with an appropriate amine, i.e. of a general formula $H_2N$—$R_5$, under conditions sufficient to form an amide bond, optionally followed by purification in order to obtain the desired configuration of the C-5 sterogenic center. Suitable conditions for the amide bond formation are known to the person skilled in the art, and are for example described in Sandham (Tetrahedron Letters, 2000, 41, 10091-10094), referred to above.

More directly, the nitrogen-containing compounds of formula (7) or (8), or a mixture thereof, are reacting with a compound according to formula (2)

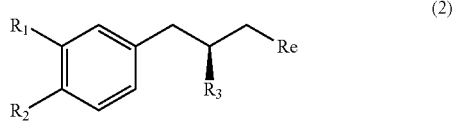

wherein $R_1$, $R_2$, and $R_3$ and Re have the aforementioned meaning, which reaction results in the synthesis of a compound according to formula (9a) or (11a), or a mixture thereof.

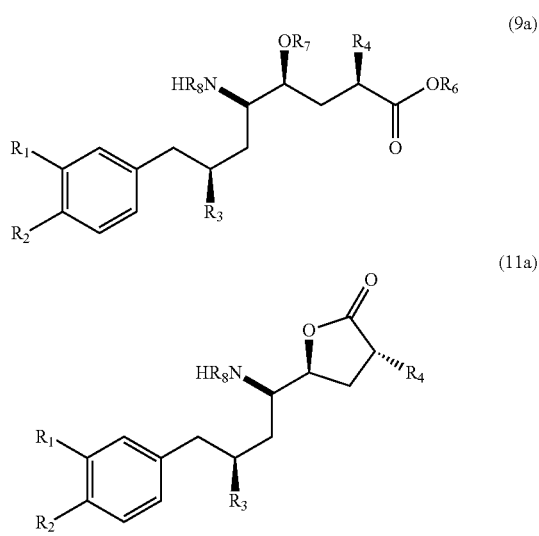

Herein, $R_1$, $R_2$, $R_3$, $R_4$, $R_6$, $R_7$, and $R_8$ have the previously given meanings.

When compounds according to formula (7a-g) or compounds according to formula (8a-g), or a mixture thereof, are reacting with compound of formula (2) the Re group denotes preferably $M(X)_n$, or $MM'(X)_n(Y)_n$. Optionally, compounds according to formula (7a-g) or compounds according to formula (8a-g), or a mixture thereof, are reacting with compound according to formula (2) in the presence of a metal complex, preferably a metal complex used in catalytically amounts, and optionally in the presence of an additive. Said catalysts can be any metal complex, preferably transition metal complexes, more preferred metal complexes derived from group VII and group VIII of the periodic system, most preferred manganese or iron complexes are used, such as $MnCl_2$, and $FeCl_3$, $Fe(acac)_3$, $FeCl_2$.

Suitable additives are Lewis acids, such as $ZnCl_2$, CuCl; CuI, $InCl_3$, $TiCl_4$, alkali metal salts, such as LiCl; tertiary amines and tertiary diamines, such as $Et_3N$, N-methylpyrrolidine, tetramethylendiamine (TMEDA); amides and ureas, such as N-methylpyrrolidinone (NMP) and 1,3-dimethyl-2-oxohexahydropyrimidine (DMPU); hexamethylphosphoric acid triamide (HMPA); tris(dialkylamino)phosphines, such as tris(dimethylamino)phosphine (HMPT).

Said metal complexes or additives can be chiral to enhance the amount of compound of formula (9a) or (11a) or mixture thereof, with the desired configuration at the C-5 stereogenic center. Chiral metal complexes can be prepared beforehand or prepared in situ, by mixing the metal complex with an suitable chiral ligand. Suitable chiral ligands are known to the person skilled in the art, for example chiral amino alcohols, optionally alkylated at the amine functionality, such as ephedrine; chiral phosphor containing compounds, such as (3,5-dioxa-4-phosphacyclohepta[2,1-a;3,4-a']dinapthalen-4-yl) dimethylamine (MonoPhos), chiral bisphosphines, such as 2,2'-Bis(di-p-tolylphosphino)-1,1'-binaphthyl (BINAP).

Suitable chiral additives are any additive mentioned above with a stereogenic center or other form of chirality. Preferred are chiral amines and amine derivatives, such as N,N-dimethylamino acid methyl esters, N,N-dimethylmethylbenzylamine and chiral phosphor containing compounds, such as (3,5-dioxa-4-phosphacyclohepta[2,1-a;3,4-a']dinapthalen-4-yl)dimethylamine (MonoPhos).

When the compound according to formula (7h) or the compound according to formula (8h), or a mixture thereof, is reacting with compound of formula (2) the Re group denotes preferably Cl, Br, I, or $OR_9$, wherein $R_9$ is a group capable of making $OR_9$ a leaving group, such group being known to the person skilled in the art, for example $R_9$ is acetyl, trifluoroacetyl; $CF_3SO_2$, $CH_3SO_2$, $CH_3C_6H_4SO_2$, $C(O)OCH_3$, or $C(O)OC_4H_9$, and this reaction is performed in the presence of a base, or metal complex. Suitable bases are any base capable of, optionally partly, deprotonating the carbon center with the nitro group directly attached to it, such as bases are known to the person skilled in the art, for example sodium hydride, sodium methoxide, n-butyllithium, sec-butyllithium, tertiar-butyllithium, KOtertiar-butyl, KOAc, KOH, NaOH, and so on. Suitable metal complexes are similar complexes as used for the synthesis of compounds of formula (7h) or (8h) or mixture thereof, as also described in Boruwa et al. in Tetrahedron Asymmetry 2006, 17, 3315-3326 and references therein.

Said bases or metal complexes can be chiral to enhance the amount of compound of formula (9a) or (11a) or mixture thereof, with the desired configuration at the C-5 stereogenic center. Suitable chiral bases are for example alkali-metal amides, such as chiral lithium amides similar to those described in Cailleau et al. Org. Biomol. Chem. 2007, 5, 3922-3931 and references therein.

With reference to producing a compound satisfying formula (1), it will be apparent that the corresponding compound of formula (9a) or (11a), or a mixture thereof, is formed with an undefined configuration at the C-5 stereogenic center (the carbon center with the $HR_8N$ moiety attached to it). It will be appreciated that the nitrogen-containing compounds of formula (7) or (8), or mixture thereof, employed in the synthesis of compound of formula (9a) or (11a), or mixture thereof, are able to react with a compound of formula (2) in a diastereoselective manner, due to a preferential direction of attack during the coupling reaction and the presence of neighbouring fixed stereogenic centers. The diastereoselectivity is influenced by the nature of the reagents of formula (7a-h), (8a-h) and (2), optionally, by the addition of a catalyst, base, and/or additive as described above. Optionally, the diastereoselectivity can be increased by making use of the different physical properties of the diastereoisomers (e.g. preferential crystallization), or by means of classic or separating moving beds (SMB) chromatography as described above. Optionally this additional purification is performed in the presence of a suitable agent capable of racemising the C-5 center. The racemization could be done in the same vessel or by external loops.

In the case of the compound according to formula (7h) or the compound according to formula (8h), or a mixture thereof, reacting with compound of formula (2) the intermediate compound obtained of formula (12) or (13) or mixture thereof is in particular suitable for preferential crystallization and racemisation (in the presence of a suitable base).

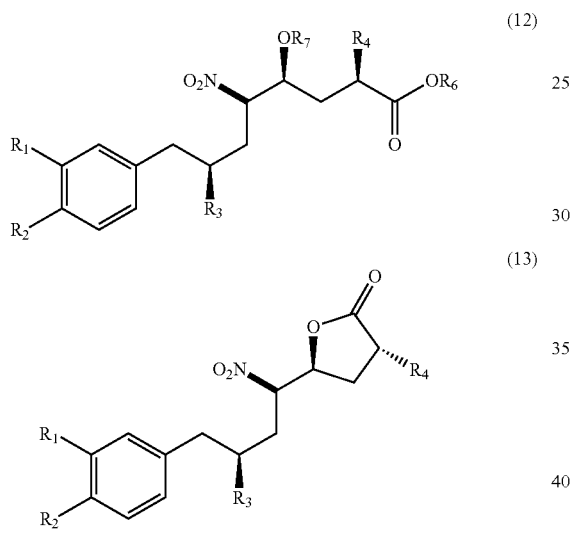

Said techniques to obtain a theoretical 100% yield of the desired enantiomer, or diastereomer using racemising techniques and techniques and/or reactions to take out the desired enantiomer or diastereomer from the reaction mixture, are well known by the person skilled in the art. Said techniques are called dynamic kinetic resolution techniques, see for example described by Pelliessier, Tetrahedron 2003, 59, 8291-8327, and references therein.

The compounds of formula (2), with $R_1$, $R_2$, $R_3$, as described above, and with Re is Cl can be made in known ways. References in this respect are Sandham et al. Tetrahedron Lett. 2000, 41, 10091-10094 and Sturm et al. Adv. Synth. Catal. 2003, 345, 160-164.

The preparation of the corresponding Grignard reagent (Re=MgCl) is described by Sandham. The preparation of many other organometallic compounds can be performed by the transmetalation reaction of the appropriate metal salts with a magnesium or lithium organometallic compound of formula (2). These transmetallation procedure are known to persons skilled in the art.

As a part of the invention, the coupling of the organometallic reagent according to formula (2) with the nitrogen containing compound of formula (7a) or formula (8a), or a mixture thereof, can be performed as depicted in the Scheme III:

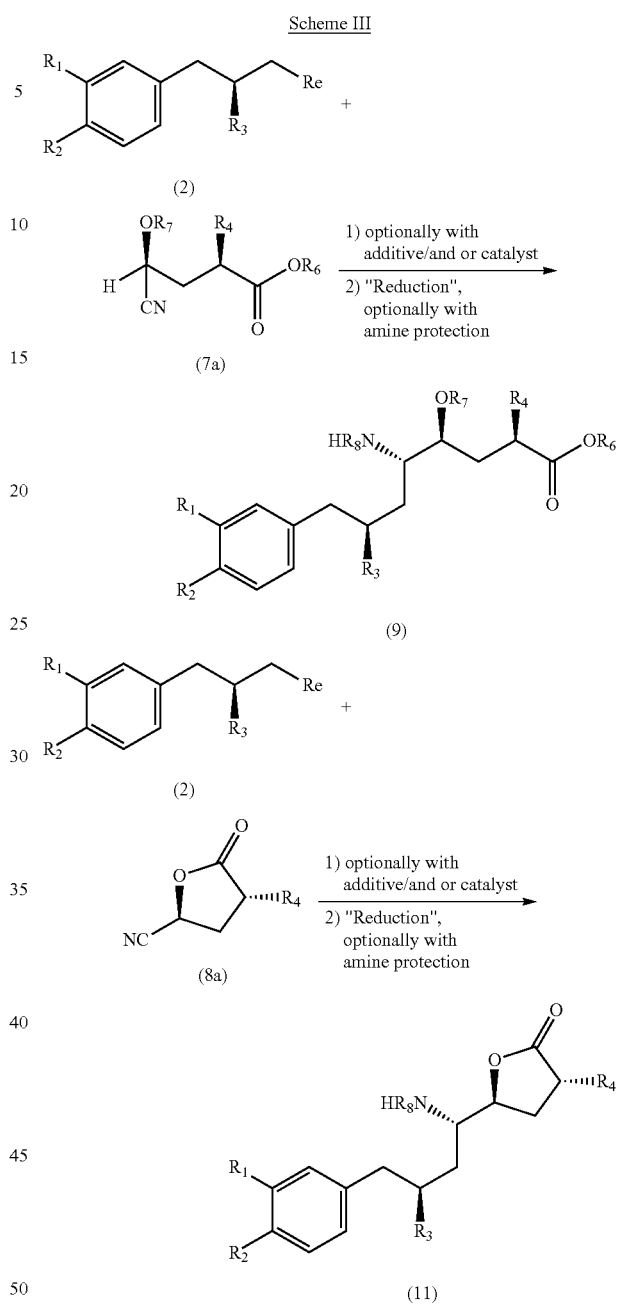

or for example by first reducing the cyanohydrin and the lactone nitrile to the corresponding iminium ions of formula (7e) and (8e), as depicted in Scheme IV.

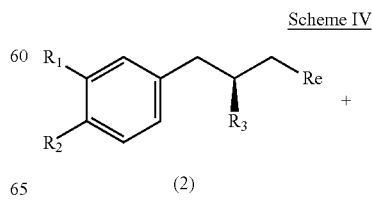

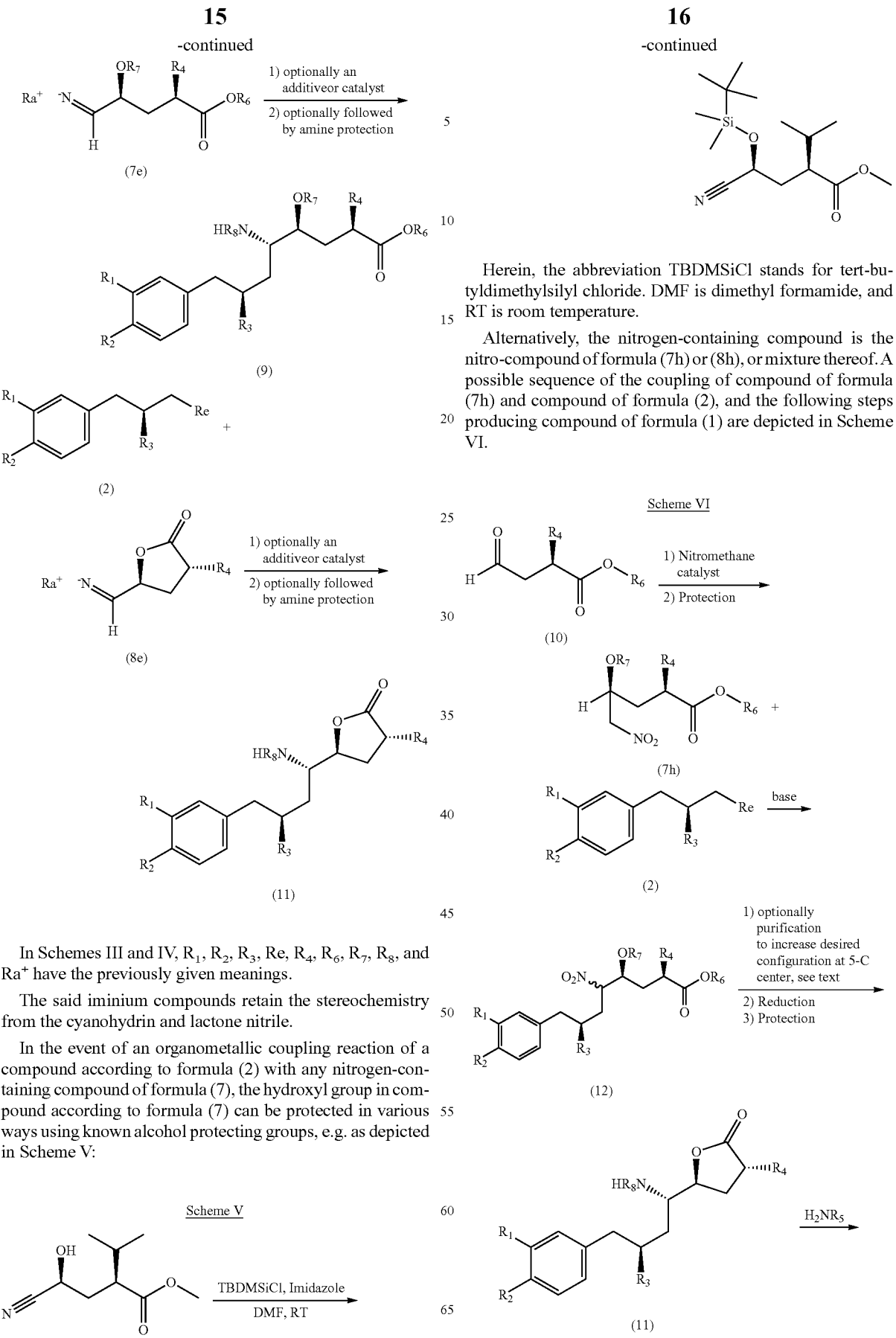

Herein, the abbreviation TBDMSiCl stands for tert-butyldimethylsilyl chloride. DMF is dimethyl formamide, and RT is room temperature.

Alternatively, the nitrogen-containing compound is the nitro-compound of formula (7h) or (8h), or mixture thereof. A possible sequence of the coupling of compound of formula (7h) and compound of formula (2), and the following steps producing compound of formula (1) are depicted in Scheme VI.

In Schemes III and IV, $R_1$, $R_2$, $R_3$, Re, $R_4$, $R_6$, $R_7$, $R_8$, and $Ra^+$ have the previously given meanings.

The said iminium compounds retain the stereochemistry from the cyanohydrin and lactone nitrile.

In the event of an organometallic coupling reaction of a compound according to formula (2) with any nitrogen-containing compound of formula (7), the hydroxyl group in compound according to formula (7) can be protected in various ways using known alcohol protecting groups, e.g. as depicted in Scheme V:

-continued

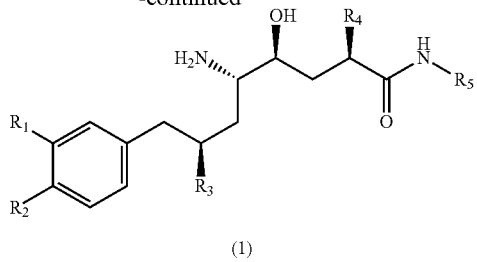

(1)

Here, $R_1$, $R_2$, $R_3$, Re, $R_4$, $R_6$, $R_7$, and $R_8$ have the previously given meanings.

As an alternative, a variant of a compound of formula (2) is used that itself does not possess the desired chirality, yet. This refers to a compound of formula (2a), which has the advantage of being more reactive:

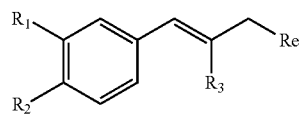

(2a)

The coupling of this compound of formula (2a) can be performed with any of the compounds of formula (7), and formula (8), or a mixture thereof. The required chirality at C-7 of compound of formula (1) can then later be introduced through hydrogenation of the C=C double bond (as for example shown for compound of formula (14) in Scheme VII). Said hydrogenation can be performed with any reducing agent, e.g. $NaBH_4$, $BH_3$, $LiAlH_4$; or hydrogen gas, optionally in the presence of a catalyst. Said catalyst can be a well known heterogeneous catalyst, such as Pd on Carbon or any support, or can be a homogeneous catalyst, e.g. those based on late transition metals, such as Rh, Ru, Ir, or Pd. Optionally, a chiral hydrogenation reagent, or a chiral catalyst is used. Said chiral catalyst can be any transition metal with a chiral ligand, or of any enzymatic origin, or the so-called organo-catalysts. Suitable chiral catalysts, are for example heterogeneous Pd on Carbon with cinchonidine alkoloids, or homogeneous rhodium complexes with chiral ligands, or for example enzymes called reductases. Suitable chiral ligands for the homogeneous catalysts are known in the art, for example chiral phosphor-containing ligands such as BINAP, JosiPhos, ChiraPhos, MonoPhos.

An alternative synthesis route to compound of formula (1) could for example satisfy the following reaction scheme VII (here shown for the reaction of compounds (2a) and (8e)):

Scheme VII

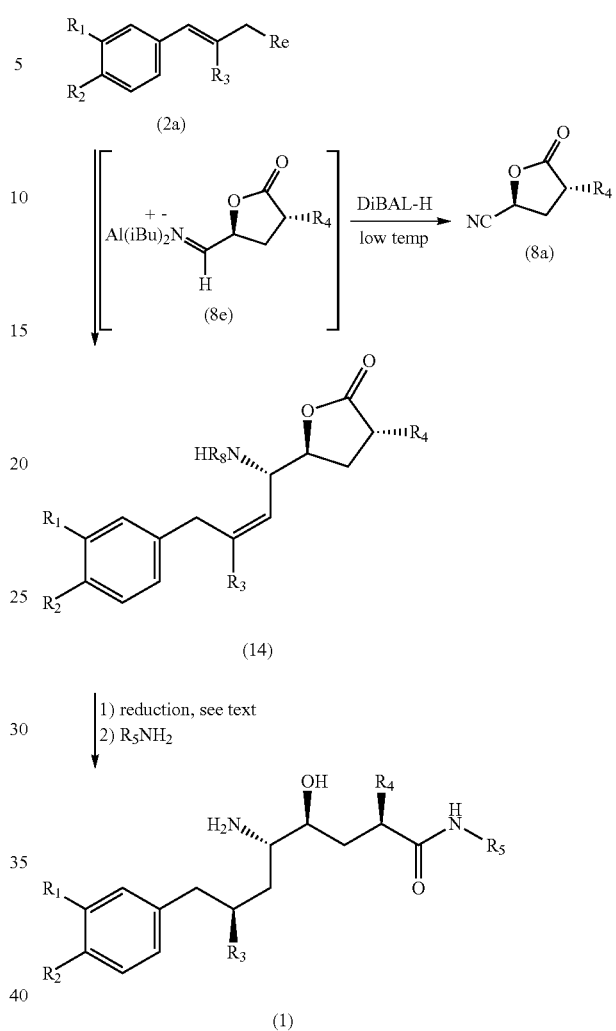

Herein, $R_1$, $R_2$, $R_3$, Re, $R_4$, and $R_8$ have the previously given meanings.

Preferably Re in compound of formula (2a) is M(X)n with the meanings for M, X and n as given above, more preferably M is Ba.

The coupling reaction of compound of (2a) with compound of formula (7) or compound of formula (8), or mixture thereof, is performed preferably according to as described above for the coupling of compound of formula (2) with compound of formula (7) or compound of formula (8), or mixture thereof.

The nitrogen-containing compound of formula (7a) can be obtained in many different ways and is part of the invention. For example the following route depicted in Scheme VIII can be used:

Scheme VIII

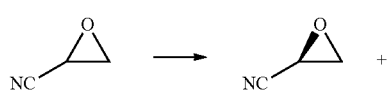

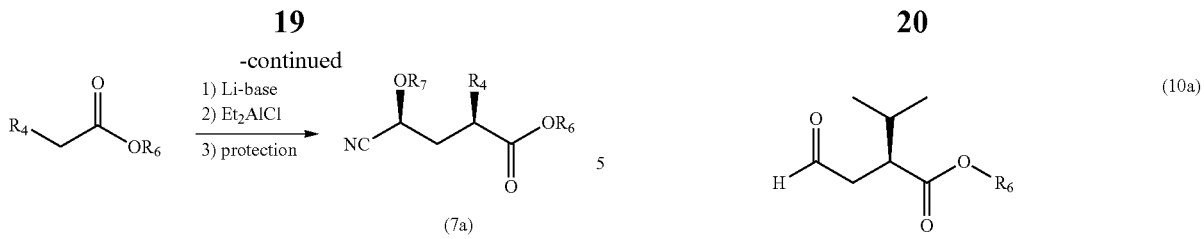

(7a)

The chiral lactone nitrile (8a), also being part of the invention can be made in various ways, e.g. according to Scheme IX:

Scheme IX

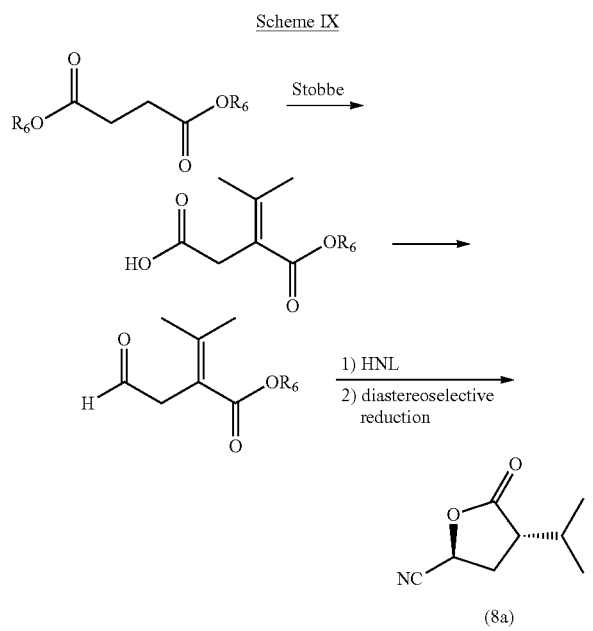

(8a)

In Schemes VIII and IX the R groups have the meanings given above.

Preferably, the nitrogen-containing compound of formula (7), or formula (8), or mixture thereof, is obtained via a novel chiral aldehyde compound as depicted below in figure (10), allowing the enantioselective addition of HCN, or related reagents, or allowing the addition of nitromethane, as mentioned above.

The Chiral Aldehyde

This refers to a compound that is useful as a precursor for the nitrogen-containing compounds, and that is a novel compound, representing a conceptually different synthetic route, in the preparation of compounds of formula (1). The chiral aldehyde satisfies the following formula (10):

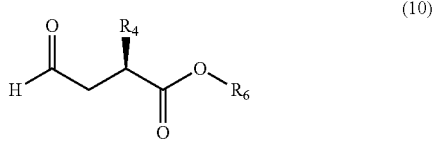

(10)

With $R_4$ and $R_6$ as indicated above. More particularly, the aldehyde intermediate provides a building-block for aliskiren, as can be used in the synthesis thereof, and then satisfies formula (10a):

(10a)

The use of the chiral aldehyde of formula (10) or formula (10a) are representing a novel approach to the synthesis of compounds of formula (1), and particularly of aliskiren. It has an advantage in the sense that it introduces the desired stereochemistry at the C-2 stereogenic center atom of compounds of formula (1) without the use of stochiometric amounts of relative expensive chiral auxiliaries as shown in Sandham et al. Tetrahedron Lett. 2000, 41, 10091-94.

The chiral aldehyde of formula (10) exhibits a further advantage in that it introduces immediately the required nitrogen in a stereochemically desired way by catalytic addition of HCN, or related reagents, or the stereochemically desired addition of nitromethane, both approaches as discussed above in connection with the synthesis of the nitrogen-containing compounds of formula (7) and (8), or a mixture thereof. Thus, the aldehyde can be converted into compound of formula (8a), optionally via compound of formula (7a).

By way of example, the following scheme (Scheme X) illustrates the HNL catalyzed addition of HCN to the chiral aldehyde (10) forming compound of formula (7a), followed by acid catalyzed lactonisation to compound of formula (8a).

Scheme X

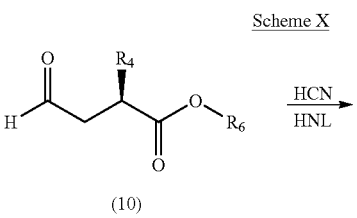

(10)

(7a)

(8a)

The chiral aldehyde itself can be obtained in various alternative ways, e.g. as depicted in the following Schemes XI (a) through XI (g); wherein, the specific compounds chosen are illustrative, and can be translated to the corresponding other aldehydes commensurate with the respective structural part of the compounds of formula (1).

Scheme XI

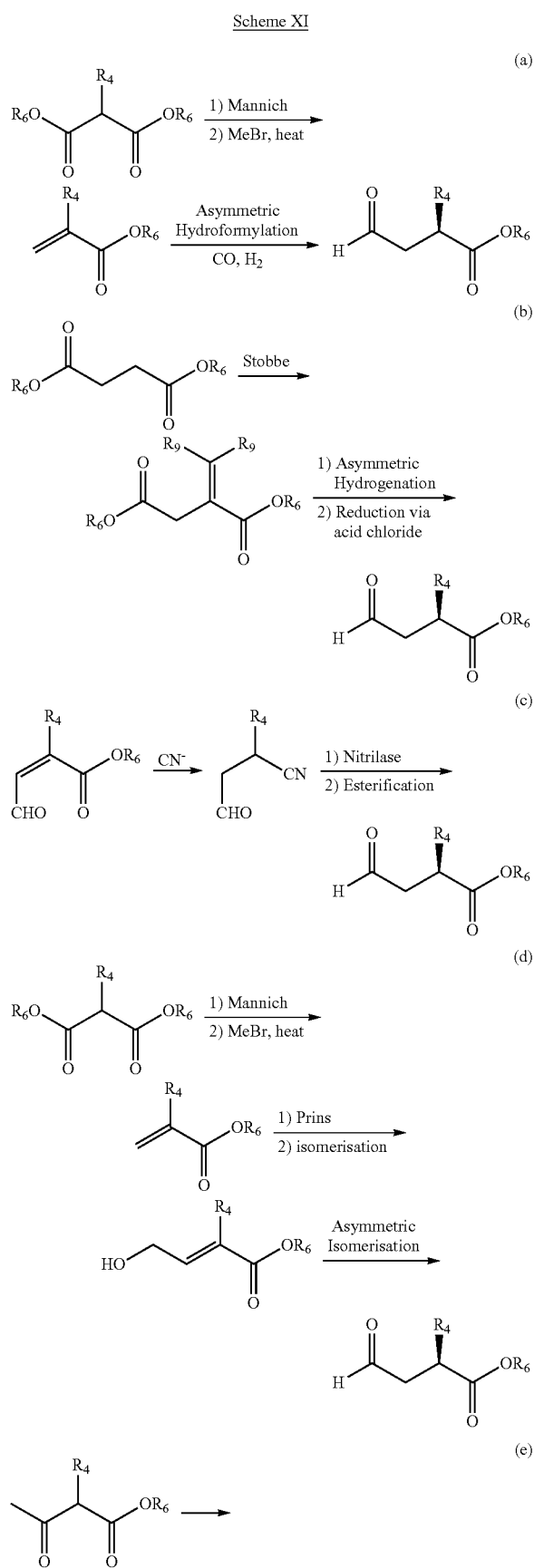

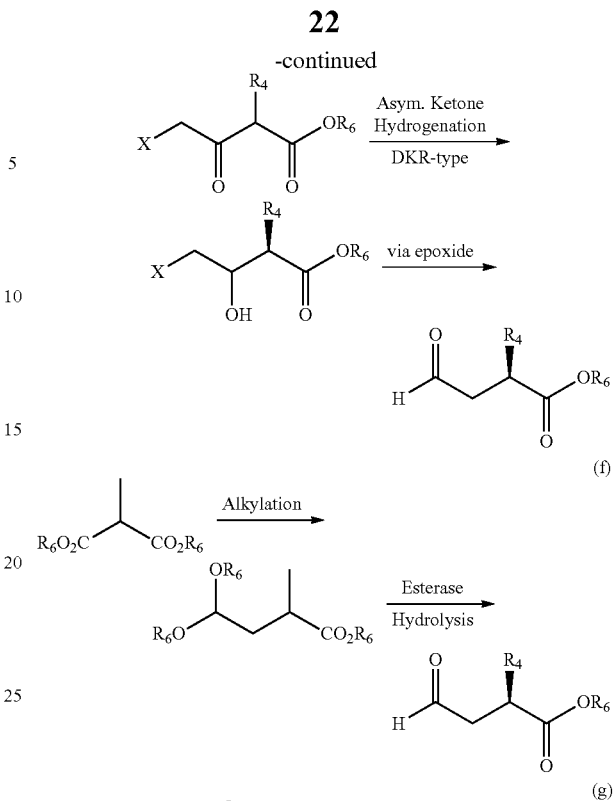

Wherein R in Scheme XI (g) denotes a H, $C_{1-6}$ alkyl, or Cl. The oxidation depicted in Scheme XI (g) could also be performed by ozonolysis. Alternatively, the chiral aldehyde can be synthesized using a chiral pool strategy, for which several options are available, e.g. from the required enantiomer of Valine or Carvone.

The various reaction steps are identified with reference to terminology and names commonly known in the art, and to the person skilled in the art are understandable as such.

Overall Synthesis

The aforementioned compounds can be used in a convergent synthesis route to the compounds of formula (9) or (11), or a mixture thereof, and ultimately to the compounds of formula (1), preferably aliskiren.

The convergence, resulting in a compound of formula (9) or (11) or mixture thereof, comes when the intermediates representing the aromatic part are reacted with the nitrogen-containing intermediate. Other than in previous routes which lead to an excess of the desired diastereomer, at the convergence stage of this invention the critical 5-amino nitrogen is already present in the molecule. Moreover, provided that the preferred choices are made in the synthetic route from the aforementioned chiral aldehyde, the amino group is present in the desired stereomeric configuration.

The compound of formula (9) can be converted into the desired end-product, such as a compound according to formula (1), by allowing it to react with the appropriate amine $NH_2$—$R_5$, optionally followed by hydrolysis of the amine protecting group. Such reactions have been described, e.g in WO 2007/039183 and WO 2006/131304. It will be apparent to the skilled person that in the event of the synthesis of aliskiren, this amine will satisfy formula (15), and be synthesized in a known manner.

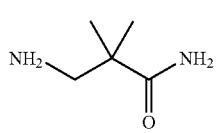

(15)

Thus, a straightforward convergent synthesis results, without undue complexity. The two aforementioned building blocks are provided, coupled and, subsequently, with one or two steps the desired end-product results.

In the case of optionally substituted groups are mentioned or used in the invention, optionally substituted groups do mean all the groups possible which will not interfere with the aimed reaction and/or reactions afterwards.

Salts

As mentioned above in respect of aliskiren, the compounds of formula (1) include salts, especially pharmaceutically acceptable salts. In view of the close relationship between the compounds and intermediates in free form and in the form of their salts, including those salts that can be used as intermediates, for example in the purification or identification of the compounds or salts thereof, any reference to "compounds", "precursors" and "intermediates" is to be understood as referring also to one or more salts thereof or a mixture of a corresponding free compound, intermediate or starting material and one or more salts thereof, each of which is intended to include also any solvate, metabolic precursor such as ester or amide of the compound of formula (1), or salt of any one or more of these, as appropriate and expedient and if not explicitly mentioned otherwise. Different crystal forms may be obtainable and then are also included.

Salts, including pharmaceutically acceptable salts are known and described in U.S. Pat. No. 5,559,111, column 11 line 50 to column 12, line 35, and incorporated herein by reference.

General Process Conditions

The following, in accordance with the knowledge of a person skilled in the art about possible limitations in the case of single reactions, applies in general to all processes mentioned in the foregoing description, or hereinafter in the Examples and Claims, while reaction conditions specifically mentioned above or below are preferred:

All the above-mentioned process steps can be carried out under reaction conditions that are known per se, preferably those mentioned specifically, in the absence or, customarily, in the presence of solvents or diluents, preferably solvents or diluents that are inert towards the reagents used and dissolve them, in the absence or presence of catalysts, condensation or neutralizing agents, for example ion exchangers, such as cation exchangers, e.g. in the $H^+$ form, depending on the nature of the reaction and/or of the reactants at reduced, normal or elevated temperature, for example in a temperature range of from about −100° C. to about 190° C., preferably from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

The solvents, from which those solvents that are suitable for any particular reaction may be selected, include those mentioned specifically or, for example, water; esters, such as lower alkyl-lower alkanoates, for example ethyl acetate; ethers, such as aliphatic ethers, for example diethyl ether, or cyclic ethers, for example tetrahydrofurane or dioxane; liquid aromatic hydrocarbons, such as benzene or toluene; alcohols, such as methanol, ethanol or 1- or 2-propanol, nitriles, such as acetonitrile; halogenated hydrocarbons, e.g. as methylene chloride or chloroform; acid amides, such as dimethylformamide or dimethyl acetamide; bases, such as heterocyclic nitrogen bases, for example pyridine or N-methylpyrrolidin-2-one; carboxylic acid anhydrides, such as lower alkanoic acid anhydrides, for example acetic anhydride; cyclic, linear or branched hydrocarbons, such as cyclohexane, heptane or (iso)pentane; or mixtures of these, for example aqueous solutions, unless otherwise indicated in the description of the processes. Such solvent mixtures may also be used in working up, for example by chromatography or partitioning. Where required or desired, water-free or absolute solvents can be used.

Where required, the working-up of reaction mixtures, especially in order to isolate desired compounds or intermediates, follows customary procedures and steps, e.g. selected from the group comprising but not limited to extraction, neutralization, crystallization, chromatography, evaporation, drying, filtration, centrifugation and the like. The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the process of the present invention those starting materials are preferably used which result in compounds of formula (1) which are described as being preferred. Special preference is given to reaction conditions that are identical or analogous to those mentioned in the Examples. The invention relates also to novel starting compounds and intermediates described herein, especially those leading to compounds mentioned as preferred herein.

It is to be understood that the invention is not limited to the embodiments and formulae as described hereinbefore. It is also to be understood that in the claims the word "comprising" does not exclude other elements or steps. Where an indefinite or definite article is used when referring to a singular noun e.g. "a" or "an", "the", this includes a plural of that noun unless something else is specifically stated.

The invention will be illustrated with reference to the following, non-limiting Examples.

Example 1

Preparation of the Grignard Reagent with Formula (2) where Re=MgCl

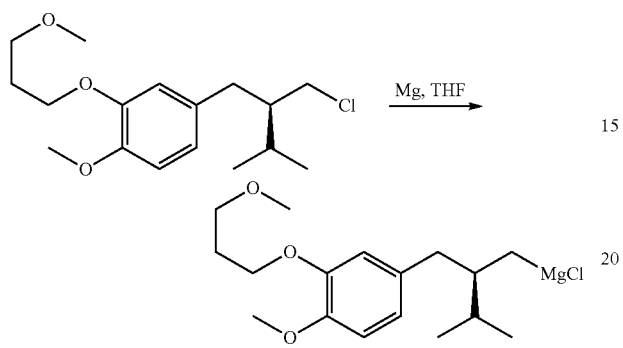

A solution of the aromatic chloride (7.87 g, 25.0 mmol) and 1,2-dibromoethane (50 μL) in THF (24 mL) was added dropwise, under a nitrogen atmosphere, to an over-dried round bottomed flask containing a suspension of magnesium powder (670 mg, 27.5 mmol, 1.1 eq.) and few crystals of $I_2$ in THF (1 mL). The temperature was maintained at 65-69° C. during the addition and for the following 2 hours, after which time the stirring was stopped and the mixture was allowed to reach room temperature overnight.

After treatment with a saturated aqueous solution of $NH_4Cl$, a sample of reaction mixture was analyzed by $^1$H-NMR and showed full consumption of the starting material. Before use, the titration of the grignard reagent was performed using sec-BuOH in the presence of 1,10-phenantroline. The titer was generally found to be 0.71-0.82 M.

Example 2

Preparation of 2-(3-methoxypropoxy)-4-((R)-2-(iodomethyl)-3-methylbutyl)-1-methoxybenzene

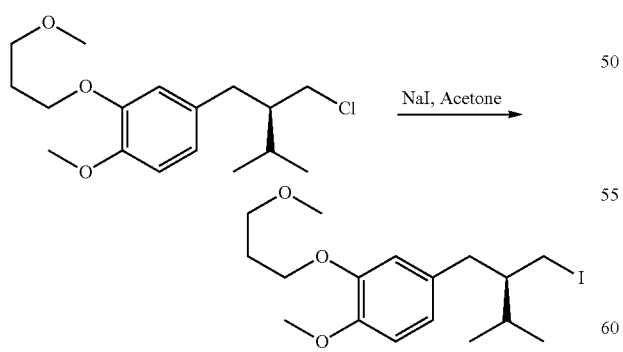

A solution of the aromatic chloride (9.5 g, 30.0 mmol) in acetone (30 mL) containing NaI (9.0 g, 60.0 mmol, 2 eq.) was stirred at room temperature for 5 days. A sample analyzed by $^1$H-NMR showed a ratio of 40:60 between starting material and product. The solvent was then removed and water was added. The aqueous layer was extracted with diethyl ether. The organic layer was washed with brine, dried over $Na_2SO_4$ and the solvent removed under reduced pressure. Acetone (30 mL) was added to the crude mixture, followed by NaI (9.0 g, 60.0 mmol, 2 eq.). The reaction mixture was stirred at 56° C. for extra 5 days. It was decided to stop the reaction when a ratio of 92:8 was reached. The work up was performed as previously described. The crude mixture was purified by flash column chromatography on silica gel affording the desired compound in 80.5% yield, as a light brown solid.

$^1$H-NMR (400 MHz, $CDCl_3$): δ 6.76-6.62 (m, 3H), 4.05 (t, J=6.5 Hz, 2H), 3.76 (s, 3H), 3.51 (t, J=6.1 Hz, 2H), 3.28 (s, 3H), 3.18-2.97 (m, 2H), 2.75-2.65 (m, 1H), 2.34-2.21 (m, 1H), 2.10-1.98 (m, 2H), 1.73-1.57 (m, 1H), 1.15-1.05 (m, 1H), 0.94 (d, J=6.5 Hz, 3H), 0.87 (d, J=6.9 Hz, 3H).

Example 3

Preparation of a Compound with Formula (2) Where Re=Li

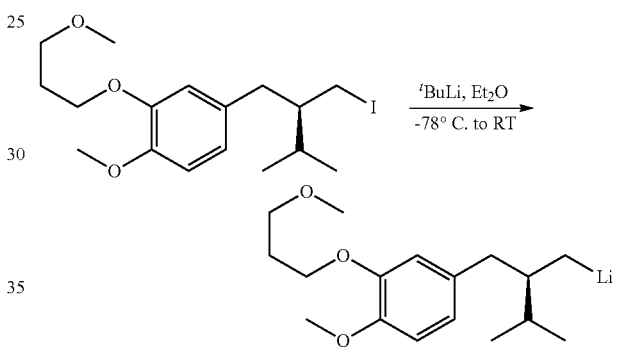

In an oven-dried flask kept under a nitrogen atmosphere, the aromatic iodide (406.3 mg, 1.0 mmol) was dissolved in diethyl ether (2.5 mL) and the solution was cooled to −78° C. A pentane solution of t-BuLi (1.7 M, 0.7 mL, 1.2 eq.) was then added dropwise and the reaction mixture was stirred for 1 h at −78° C., after which time it was allowed to reach room temperature and it was stirred for an extra hour. A sample was quenched by the addition of an aqueous HCl solution (3 M), which was extracted with ethylacetate. The organic layer was dried over $Na_2SO_4$, the solvent was removed and the residue was analyzed by $^1$H-NMR, revealing full conversion of the starting material and presence of 73.0% of the hydrolysis compound related to the desired product.

Example 4

Preparation of chiral aldehyde (10): (S)-methyl 2-(formylmethyl)-3-methylbutanoate

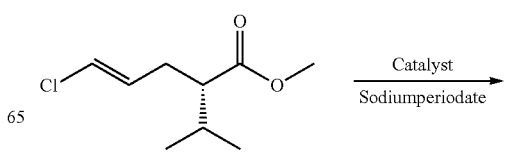

-continued

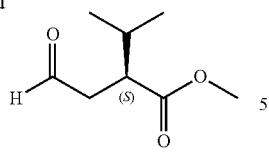

In a 1 ltr Schott-bottle with magnetic stirrer 18 g of (S,E)-methyl 5-chloro-2-isopropylpent-4-enoate (0.094 mol) was mixed with 680 ml of acetonitrile and 88 ml of water and it was stirred at 25° C. To this solution 39.6 g of NaIO$_4$ (0.184 mol) and 1.08 g of RuCl$_3$×H$_2$O were added at once. The temperature was maintained at 35° C. The progress of the reaction was followed by TLC (eluent: heptane/ethylacetate 3/2).

When the reaction was finished the mixture was cooled to RT and the precipitate was filtered off and washed with ethylacetate. The organic liquid phase was successively washed once with 50 ml of a saturated aqueous solution of sodium thiosulfate, once with 50 ml of brine, once with 50 ml of a saturated aqueous solution of sodium bicarbonate and once with 40 ml of brine. The organic solution was dried over Na$_2$SO$_4$. After filtering off Na$_2$SO$_4$, the organic solvent was removed under reduced pressure yielding 18.4 g of crude aldehyde.

Example 5

Synthesis of Enantiomerically Enriched hydroxy nitrile: (S)-methyl 2-((S)-2-cyano-2-hydroxyethyl)-3-methylbutanoate

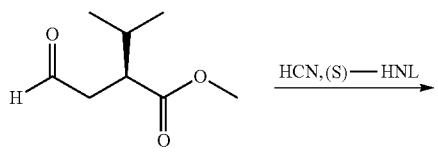

The chiral aldehyde (10) (0.033 mol) was diluted with 345 ml of toluene and 500 mL of a (S)-HNL solution (pH=5.6) was added. The two phases were mixed by stirring and, at a temperature of 0° C., 20 mL of pure HCN (0.53 mol) was dosed over 5 minutes. The mixture was stirred for 3 hours at 0° C. The conversion of the aldehyde was >94% and the enantiomeric excess of the product was 94%.

The reaction mixture was diluted with 1 L of MTBE and the aqueous layer was extracted several times with MTBE. The combined organic extracts (approximately 2.5 L) were stabilized with 0.5 mL of phosphoric acid (conc.) and concentrated under reduced pressure yielding 12.4 g of the title compound as a crude mixture which was used without further purification.

Example 6

Synthesis of the lactone nitrile: (2S,4S)-tetrahydro-4-isopropyl-5-oxofuran-2-carbonitrile

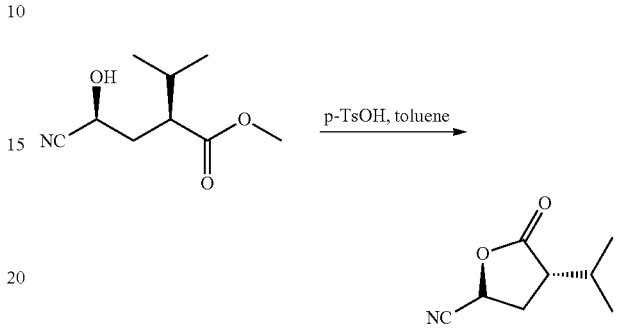

The crude cyanohydrin (12.4 g) was diluted with 120 mL of toluene and 25 g of mol sieves 5 Å were added. To this mixture, 250 mg of p-toluenesulfonic acid was added and, whilst stirring, the mixture was heated at 70° C. for 1 hour. After cooling to RT, the molecular sieves were filtered off and washed with toluene. The collected organic phase was washed with a saturated aqueous solution of sodium bicarbonate and dried over Na$_2$SO$_4$. After filtering off the Na$_2$SO$_4$, the organic phase was concentrated under reduced pressure yielding 10.7 g of crude lactone. Purification by flash column chromatography on silica gel yielded the title compound with >98% purity.

$^1$H-NMR (400 MHz, CDCl$_3$): δ 5.11 (dd, J=8.4, 2.3 Hz, 1H), 2.84-2.74 (m, 1H), 2.62-2.41 (m, 2H), 2.31-2.16 (m, 1H), 1.10 (d, J=6.9 Hz, 3H), 0.97 (d, J=6.9 Hz, 3H).

Example 7

Synthesis of the TBS-Protected cyanohydrin: (S)-methyl 2-[(S)-2-cyano-2-(t-butyldimethylsilyl)oxy-ethyl]-3-methylbutanoate

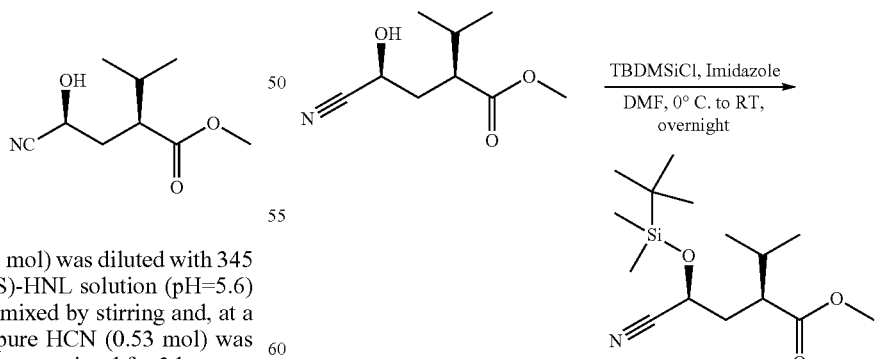

Imidazole (7.35 g, 108 mmol) was added at 0° C. to a solution of the crude hydroxyl nitrile (10 g) in DMF (180 mL), followed by TBDMSiCl (9.77 g, 64.8 mmol). The mixture was stirred at room temperature overnight. Subsequently, the reaction mixture was poured over an ice-cold aqueous HCl solution (1 M, 80 mL). After the addition of diethyl ether (100 mL), the organic layer was separated and the aqueous layer was further extracted with diethyl ether (2×100 mL). The combined organic layers were washed with a saturated aqueous solution of sodium bicarbonate and brine, dried over Na$_2$SO$_4$ and the solvent was then removed under reduced pressure. The crude mixture was purified by flash column chromatography on silica gel.

$^1$H-NMR (400 MHz, CDCl$_3$): δ 4.26 (dd, J=9.2, 3.4 Hz, 1H), 3.50 (s, 3H), 2.37-2.29 (m, 1H), 2.08-1.96 (m, 1H), 1.86-1.68 (m, 2H), 0.81-0.68 (m, 15H), 0.00 (s, 3H), −0.08 (s, 3H).

Example 8

Synthesis of N-diisobutylaluminium (2S)-methyl 4-(t-butyldimethylsilyl)oxy-5-imino-2-isopropylpentanoate

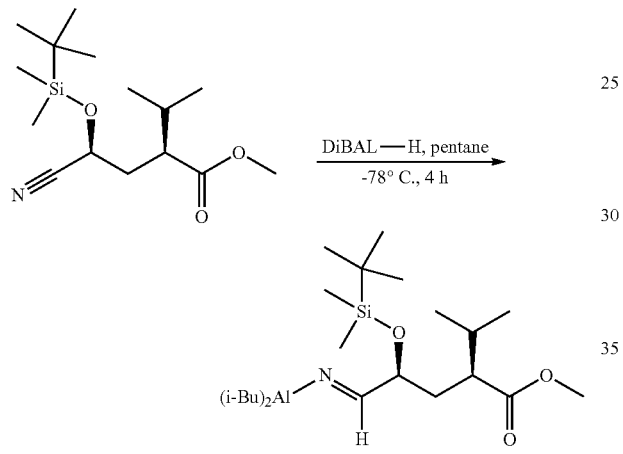

A solution of TBS-protected cyanohydrin (75 mg, 0.25 mmol) in pentane (2 mL) was cooled to −78° C. and kept under a nitrogen atmosphere. A pentane solution of DiBAL-H (1 M, 0.25 mL) was then added dropwise. The reaction mixture was stirred at −78° C. for extra 4 hours. The consumption of the starting material was followed by TLC and GC. The resulting metallo-imine was maintained at the same temperature and used without any further purification.

Example 9

Synthesis of the triethylborane-Complexed imine: (2S)-methyl 4-(t-butyldimethylsilyl)oxy-5-imino-2-isopropylpentanoate triethylborane complex

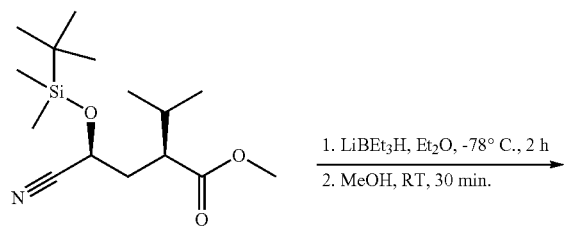

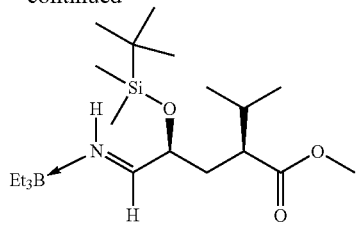

A solution of TBS-protected cyanohydrin (75 mg, 0.25 mmol) in Et$_2$O (2 mL) was cooled to −78° C. and kept under a nitrogen atmosphere. A THF solution of LiBEt$_3$H (1 M, 0.25 mL) was then added dropwise. The consumption of the starting material was followed by TLC and GC. After stirring at the same temperature for 2 hours, MeOH (10 μL, 1 eq.) was added to the reaction mixture, which was then stirred for extra 30 minutes at room temperature. The development of a light turbidity was observed, probably due to the presence in solution of MeOLi. The resulting metallo-imine was analyzed and used without any further purification.

Metallo-imine relevant peaks $^1$H-NMR (400 MHz, CDCl$_3$): δ 9.48 (m, 1H), 7.54 (m, 1H), 4.34 (m, 1H), 3.63 (s, 3H), 2.19 (m, 2H), 0.60 (t, 9H), 0.14 (q, 6H).

Example 10

Synthesis of the TBS-Protected α-hydroxy aldehyde: (S)-methyl 2-((S)-2-formyl-2-(t-butyldimethylsilyl)oxy ethyl)-3-methylbutanoate

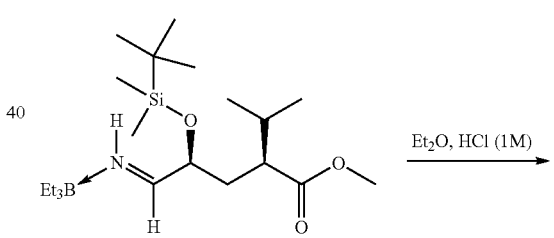

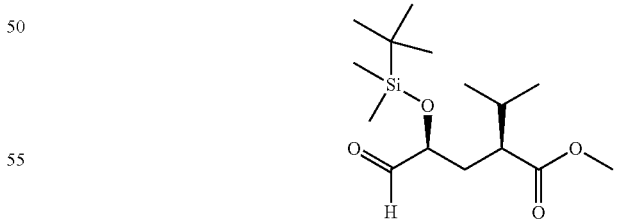

The crude solution of the previously obtained metallo-imine was treated with an aqueous HCl solution (1 M), which was extracted with diethyl ether. The organic layer was dried over Na$_2$SO$_4$, the solvent was removed under reduced pressure. Purification by flash column chromatography on silica gel yielded the title compound.

$^1$H-NMR (400 MHz, CDCl$_3$): 9.53 (d, J=1.5 Hz, 1H), 9.47 (d, J=1.9 Hz, 1H), 3.95-3.85 (m, 1H), 3.61 (s, 3H), 3.60 (s,

3H), 2.42-2.29 (m, 1H), 2.07-1.94 (m, 1H), 1.92-1.80 (m, 1H), 1.61-1.50 (m, 1H), 0.91-0.77 (m, 15H), 0.03-(−)0.04 (m, 6H).

Example 11

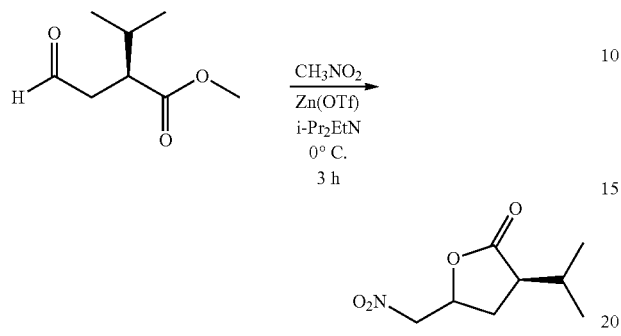

363 mg (1.0 mmol, 1.03 eq) zinctriflate, 1 ml (18.5 mmol, 19 eq) nitromethane and 174 µl (1.0 mmol, 1.03 eq) diisopropylethylamine were placed in a dry schlenk vessel under Nitrogen. The yellow slurry was cooled in ice and 153.3 mg (0.97 mmol) (S)-methyl 2-isopropyl-4-oxobutanoate was added. The reaction mixture was stirred for 3 h, after which it was quenched with 2 ml 1 N ammonium chloride solution. After separation the water phase was extracted 3 times with 4 ml dichloromethane and the combined organic phases were washed with 4 ml brine and dried with $Na_2SO_4$, yielding 365 mg crude material after film evaporation, which contained still diisopropylethylamine according to NMR. The material was dissolved in 5 ml dichloromethane, washed 3 times with 1 ml 1 N HCl, dried with sodiumsulphate yielding 161 mg after removal of the solvent. Column separation (30/70 v/v ethylacetate/heptane) gave the pure target compound (3S)-3-isopropyl-5-(nitromethyl)dihydrofuran-2(3H)-one.

The invention claimed is:

1. A method for the preparation of a compound satisfying formula (1), or a pharmaceutically acceptable salt thereof,

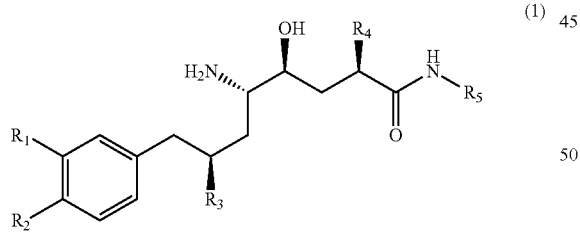

with $R_1$ being selected from the group consisting of F, Cl, Br, I, $C_{1-6}$ halogenalkyl, $C_{1-6}$alkoxy-$C_{1-6}$alkyloxy, and $C_{1-6}$alkoxy-$C_{1-6}$alkyl; $R_2$ being selected from the group consisting of F, Cl, Br, I, $C_{1-4}$alkyl or $C_{1-4}$alkoxy; $R_3$ and $R_4$ each independently being branched $C_{3-6}$alkyl; and $R_5$ being selected from the group consisting of $C_{1-12}$cycloalkyl, $C_{1-12}$alkyl, $C_{1-12}$hydroxyalkyl, $C_{1-6}$ alkoxy-$C_{1-6}$alkyl, $C_{1-6}$alkanoyloxy-$C_{1-6}$alkyl, $C_{1-12}$aminoalkyl, $C_{1-6}$ alkylamino-$C_{1-6}$ alkyl, $C_{1-6}$dialkylamino-$C_{1-6}$ alkyl, $C_{1-6}$alkanoylamino-$C_{1-6}$alkyl, HO—(O)C—$C_{1-12}$alkyl, $C_{1-6}$ alkyl-O—(O)C—$C_{1-6}$alkyl, $H_2$N—C(O)—$C_{1-12}$alkyl, $C_{1-6}$alkyl-HN—C(O)—$C_{1-6}$alkyl, ($C_{1-6}$ alkyl)$_2$-N—C(O)—$C_{1-6}$alkyl; saturated, unsaturated, or partially saturated $C_{1-12}$ heterocyclyl bonded via a carbon atom, and which heterocyclyl is optionally substituted one or more times by $C_{1-6}$alkyl, trifluoromethyl, nitro, amino, N-mono- or N,N-di-$C_{1-6}$alkylated amino, $C_{1-6}$alkanoyl, $C_{2-6}$alkenyl, $C_{2-6}$alkynyl, $C_{1-6}$ alkoxy, $C_{1-6}$alkoxycarbonylamino, $C_{1-6}$alkylcarbonylamino, $C_{1-6}$alkylcarbonyloxy, $C_{1-12}$aryl, N-mono or N,N-di-$C_{1-6}$alkylated carbamoyl, optionally esterified carboxyl, cyano, halogen, halo-$C_{1-6}$alkoxy, halo-$C_{1-6}$alkyl, $C_{1-12}$heteroaryl, saturated, unsaturated or partially saturated $C_{1-6}$heterocyclyl, hydroxyl, nitro; comprising the following steps:

a) reacting a first compound according to formula (2),

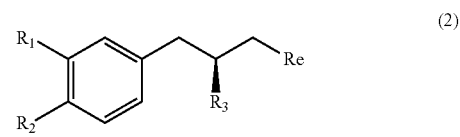

wherein $R_1$, $R_2$, and $R_3$ have the aforementioned meaning and Re denotes:

a reactive moiety selected from F; Cl; Br; I; M(X)$_n$, wherein X is F, Cl, Br, I, CN, $C_{1-12}$alkyl, or $C_{1-6}$alkoxy, M is a metal, and n is 0, 1, 2, 3, or 4; MM'(X)$_n$(Y)$_{n'}$, wherein each of M and M' is a metal, X and Y are each independently chosen from F, Cl, Br, I, or CN, $C_{1-12}$alkyl, $C_{1-6}$ alkoxy, and n, n' are each independently chosen from the values as described above for n;

or Re is OR$_9$, wherein $R_9$ is a group capable of making OR$_9$ a leaving group, with a second nitrogen containing compound satisfying either formula (7)

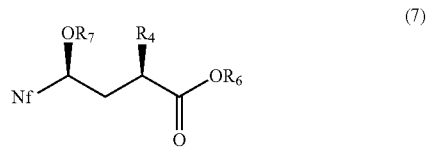

wherein $R_4$, has the meaning given above, $R_6$ represents H, or optionally substituted $C_{1-12}$alkyl, optionally substituted $C_{1-12}$alkylaryl, or optionally substituted $C_{1-12}$aryl; $R_7$ represents H, or is an O-protecting group; or $R_6$ forms with $R_7$ an, optionally substituted $C_{1-12}$(hetero)cyclic compound, as such protecting both the acid and alcohol group; Nf is a group comprising a carbon atom directly bonded to a nitrogen atom, with said compound according to formula (7) being selected from the group of compounds consisting of (7a), (7b), (7c), (7d), (7e), (7f), (7g) and (7h) and Z is a N-protecting group; $R_{11}$ is a O-protecting group; $R_{12}$ and $R_{13}$ are either the same or different fragments, chosen from the group of H, optionally substituted $C_{1-12}$alkyl, optionally substituted $C_{1-12}$alkylaryl and optionally substituted $C_{1-12}$aryl, or $R_{12}$ and $R_{13}$ are joined together in a $C_{1-20}$ (hetero)cyclic structure; Ra$^+$ is a counter-cation; St is a group capable of stabilizing the imine,

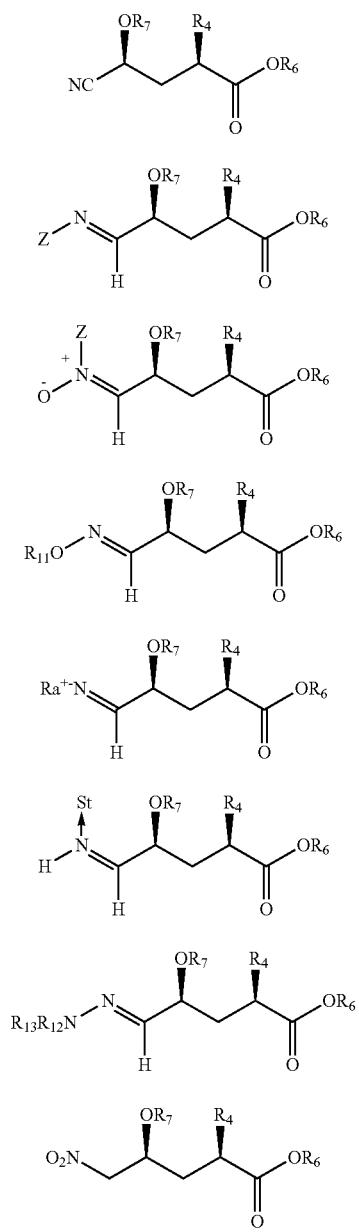

or the lactonized form thereof according to formula (8)

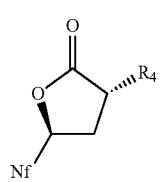

with said compound according to formula (8) being selected from the group of compounds consisting of (8a), (8b), (8c), (8d), (8e), (8f), (8g) and (8h) and wherein $R_4$, Z, $R_{11}$, $Ra^+$, St, $R_{12}$, and $R_{13}$ have the meaning given above,

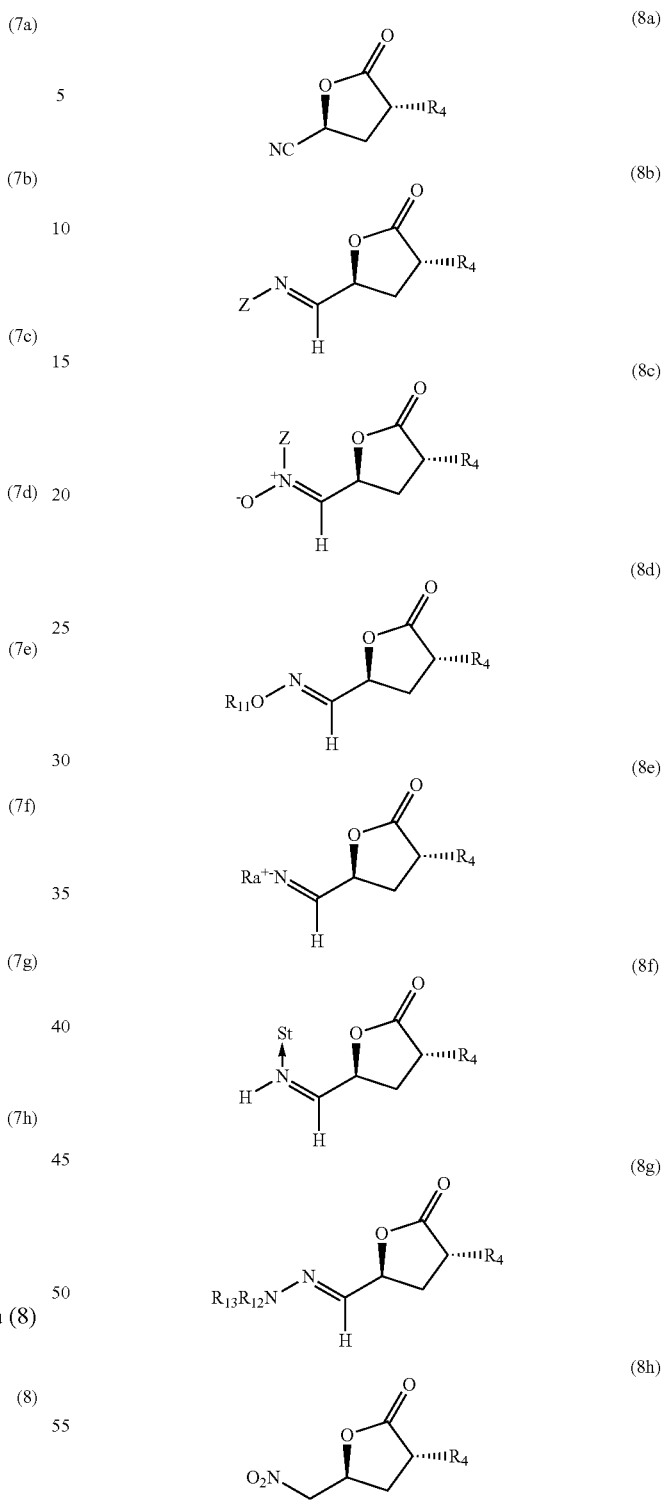

optionally in the presence of a suitable catalyst and/or an additive and/or a suitable base, also depending on the choice of Nf in the compounds according to formula (7) and/or (8), which reaction results in the formation of a compound according to formula (9a), or its lactonized form (11a) or a mixture thereof,

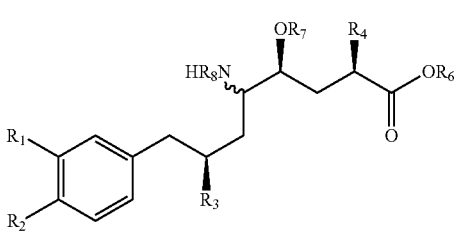
(9a)

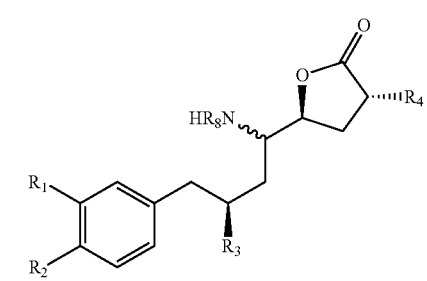
(11a)

or which reaction results in the formation of a compound according to formula (12) or its lactonized form (13) or a mixture thereof,

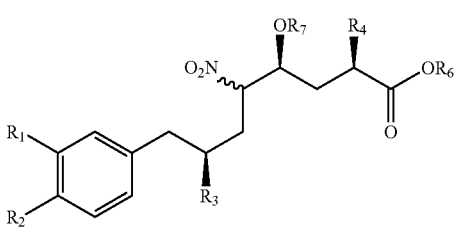
(12)

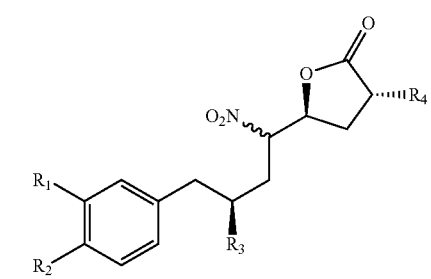
(13)

wherein the $R_1$, $R_2$, $R_3$, $R_4$ and $R_7$ groups have the same meaning as described above, and wherein $R_8$ denotes H, or a group remaining after the reaction of the Nf group as it was present in the compound of formula (7) or (8);

b) depending on the choice of Nf in the compound(s) according to formula (7) or (8), performing one or more reactions to make the moiety attached via the N-atom to the C-5 stereogenic center of the compounds (9a) and/or (11a) inactive for the reaction step c); and c) further reacting the compound according to formula (9a) and/or (11a), or a mixture thereof, or the compound according to formula (12) or (13), or mixture thereof, with an amine of the general formula $H_2N—R_5$, with $R_5$ having the meaning given above, under conditions suitable to form an amide bond.

2. A process according to claim 1 comprising the step of purifying the compound according to formula (9a), or (11a) or mixture thereof, or the compound according to formula (12) or (13), or mixture thereof, to obtain a desired diastereomeric purity for the C-5 stereogenic center.

3. A process according claim 1, comprising the step of reducing the compound according to formula (12) or (13), or mixture thereof, to obtain a compound according to formula (9a), or (11a) or mixture thereof, and subsequently a protection step to make the moiety attached via the N-atom to the C-5 stereogenic center of the compounds (9a) and/or (11a) inactive for the reaction step c).

4. A process according claim 3, comprising the step of deprotecting the moiety attached via the N-atom to the C-5 stereogenic center of the compounds (9a) and/or (11a), or a reducing step of the nitro moiety, if the reaction step c) is performed with the compound according to formula (12) or (13), or a mixture thereof.

5. A process according to claim 1, comprising isolating the compound according to formula (1), in such a way that the desired diastereomeric purity in compound of formula (1) is obtained, or by isolating any suitable salt thereof.

6. A method according to claim 1, wherein the reaction of building block of formula (2) with building block of formula (7) and/or (8), results in the formation of compound satisfying formula (9) or (11) or a mixture thereof,

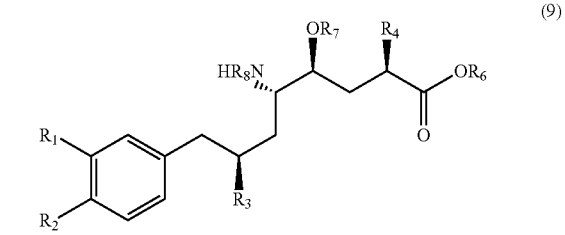
(9)

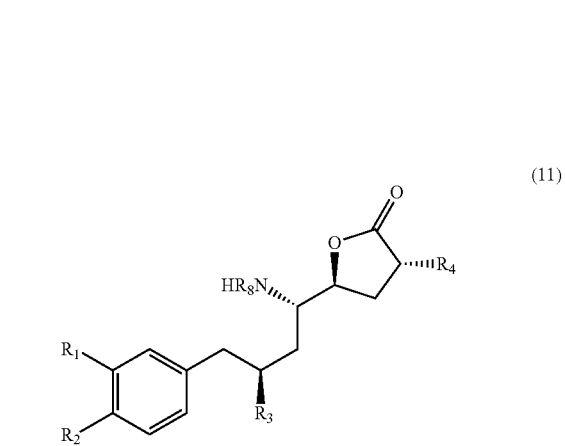
(11)

wherein the $R_1$, $R_2$, $R_3$, $R_4$, $R_6$, $R_7$, and $R_8$ groups have the same meaning as described in claim 1.

7. A method according to claim 1, wherein $R_1$ is 3-methoxy-propoxy, $R_2$ is methoxy, and $R_3$ and $R_4$ are 2-propyl.

8. A method according to claim 1, wherein the reaction of building block of formula (2) with a compound of formula (7) and/or (8), results in the formation of compound satisfying formula (9) and/or (11) or a mixture thereof

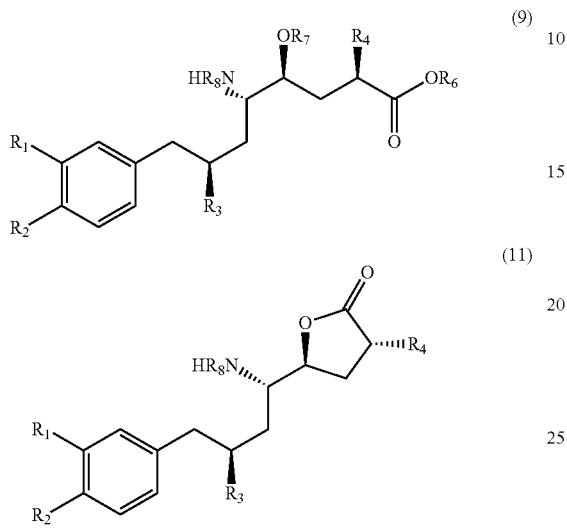

(9)

(11)

wherein the $R_1$, $R_2$, $R_3$, $R_4$, $R_6$, $R_7$, and $R_8$ groups have the same meaning as described in claim 1, and wherein the desired configuration at the C-5 stereogenic center is obtained by dynamic kinetic resolution techniques of the compound satisfying formula (9a) or (11a) or a mixture thereof, or by dynamic kinetic resolution techniques of compound according to formula (12) or its lactonized form (13) or a mixture thereof.

9. A method for the preparation of a compound satisfying formula (1), or a pharmaceutically acceptable salt thereof,

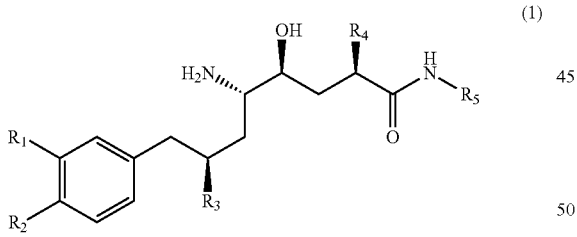

(1)

with $R_1$ is 3-methoxy-propoxy, $R_2$ is methoxy, and $R_3$ and $R_4$ are 2-propyl, and $R_5$ is selected from the group consisting of $C_{1-12}$cycloalkyl, $C_{1-12}$alkyl, $C_{1-12}$ hydroxyalkyl, $C_{1-6}$ alkoxy-$C_{1-6}$alkyl, $C_{1-6}$alkanoyloxy-$C_{1-6}$ alkyl, $C_{1-12}$-aminoalkyl, $C_{1-6}$ alkylamino-$C_{1-6}$ alkyl, $C_{1-6}$dialkylamino-$C_{1-6}$alkyl, $C_{1-6}$alkanoylamino-$C_{1-6}$ alkyl, HO—(O)C—$C_{1-12}$alkyl, $C_{1-6}$ alkyl-O—(O)C—$C_{1-6}$alkyl, $H_2N$—C(O)—$C_{1-12}$alkyl, $C_{1-6}$alkyl-HN—C(O)—$C_{1-6}$alkyl, $(C_{1-6}$ alkyl$)_2$-N—C(O)—$C_{1-6}$alkyl; saturated, unsaturated, or partially saturated $C_{1-12}$ heterocyclyl bonded via a carbon atom, and which heterocyclyl is optionally substituted one or more times by $C_{1-6}$alkyl, trifluoromethyl, nitro, amino, N-mono- or N,N-di-$C_{1-6}$alkylated amino, $C_{1-6}$alkanoyl, $C_{2-6}$alkenyl, $C_{2-6}$alkynyl, $C_{1-6}$ alkoxy, $C_{1-6}$alkoxycarbonylamino, $C_{0-6}$ alkylcarbonylamino, $C_{1-6}$alkylcarbonyloxy, $C_{1-12}$aryl, N-mono or N,N-di-$C_{1-6}$ alkylated carbamoyl, optionally esterified carboxyl, cyano, halogen, halo-$C_{1-6}$ alkoxy, halo-$C_{1-6}$alkyl, $C_{1-12}$heteroaryl, saturated, unsaturated or partially saturated $C_{1-6}$heterocyclyl, hydroxyl, nitro; comprising the following steps:

a) reacting a first compound according to formula (2),

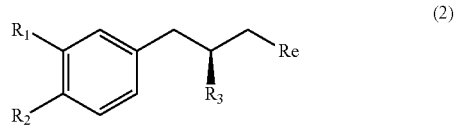

(2)

wherein $R_1$, $R_2$, and $R_3$ have the aforementioned meaning and Re denotes:

a reactive moiety selected from F; Cl; Br; I; $M(X)_n$, wherein X is F, Cl, Br, I, CN, $C_{1-12}$alkyl, or $C_{1-6}$alkoxy, M is a metal, and n is 0, 1, 2, 3, or 4; $MM'(X)_n(Y)_{n'}$, wherein each of M and M' is a metal, X and Y are each independently chosen from F, Cl, Br, I, or CN, $C_{1-12}$alkyl, $C_{1-6}$ alkoxy, and n, n' are each independently chosen from the values as described above for n;

or Re is $OR_9$, wherein $R_9$ is a group capable of making $OR_9$ a leaving group, with a second nitrogen containing compound satisfying either formula (7)

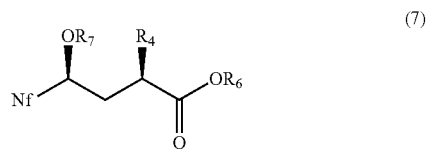

(7)

wherein $R_4$, has the meaning given above, $R_6$ represents H, or optionally substituted $C_{1-12}$alkyl, optionally substituted $C_{1-12}$alkylaryl, or optionally substituted $C_{1-12}$aryl; $R_7$ represents H, or is an O-protecting group; or $R_6$ forms with $R_7$ an, optionally substituted $C_{1-12}$(hetero)cyclic compound, as such protecting both the acid and alcohol group; Nf is a group comprising a carbon atom directly bonded to a nitrogen atom, with said compound according to formula (7) being selected from the group of compounds consisting of (7a), (7b), (7c), (7d), (7e), (7f), (7g) and (7h) and Z is a N-protecting group; $R_{11}$ is a O-protecting group; $R_{12}$ and $R_{13}$ are either the same or different fragments, chosen from the group of H, optionally substituted $C_{1-12}$alkyl, optionally substituted $C_{1-12}$alkylaryl and optionally substituted $C_{1-12}$aryl, or $R_{12}$ and $R_{13}$ are joined together in a $C_{1-20}$ (hetero)cyclic structure; $Ra^+$ is a counter-cation; St is a group capable of stabilizing the imine,

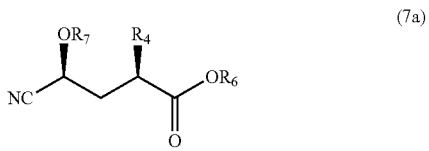

(7a)

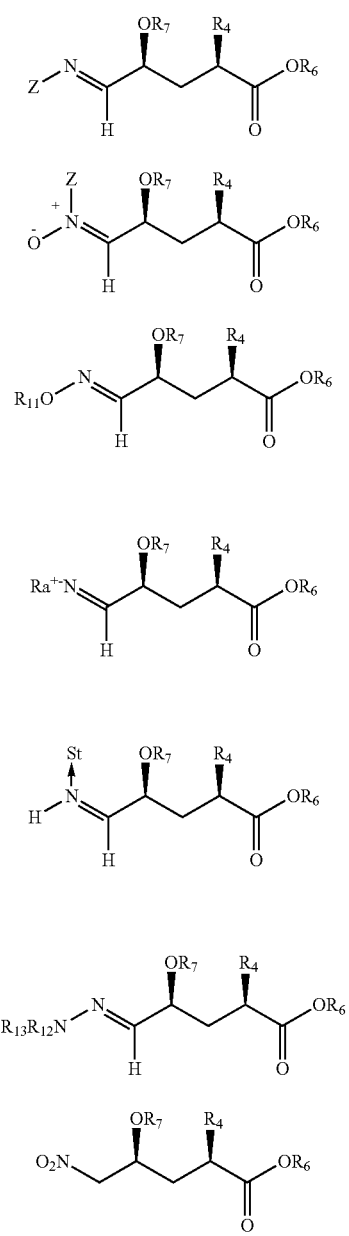

or the lactonized form thereof according to formula (8)

with said compound according to formula (8) being selected from the group of compounds consisting of (8a), (8b), (8c), (8d), (8e), (8f), (8g) and (8h) and wherein $R_4$, Z, $R_{11}$, $Ra^+$, St, $R_{12}$, and $R_{13}$ have the meaning given above, optionally in the presence of a suitable catalyst and/or an additive and/or a suitable base, also depending on the choice of Nf in the compounds according to formula (7) and/or (8), which reaction results in the formation of a compound according to formula (9a), or its lactonized form (11a) or a mixture thereof,

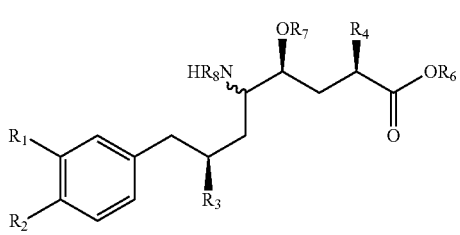

(9a)

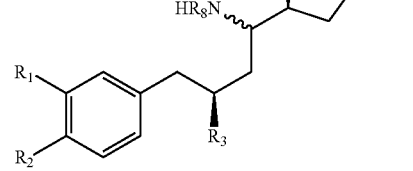

(11a)

or which reaction results in the formation of a compound according to formula (12) or its lactonized form (13) or a mixture thereof,

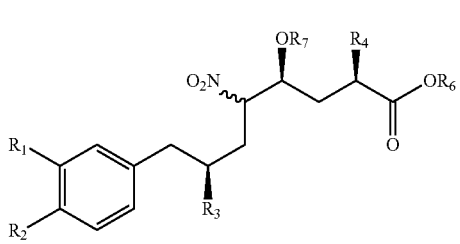

(12)

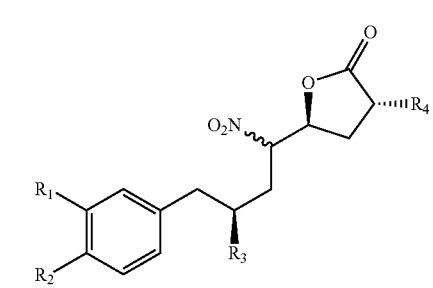

(13)

wherein the $R_1$, $R_2$, $R_3$, $R_4$ and $R_7$ groups have the same meaning as described above, and wherein $R_8$ denotes H, or a group remaining after the reaction of the Nf group as it was present in the compound of formula (7) or (8);

b) depending on the choice of Nf in the compound(s) according to formula (7) or (8), performing one or more reactions to make the moiety attached via the N-atom to the C-5 stereogenic center of the compounds (9a) and/or (11a) inactive for the reaction step c);

c) further reacting the compound according to formula (9a) and/or (11a), or a mixture thereof, or the compound according to formula (12) or (13), or mixture thereof, with an amine of the general formula $H_2N$—$R_5$, with $R_5$ having the meaning given above, under conditions suitable to form an amide bond;

d) purifying the compound according to formula (9a), or (11a) or mixture thereof, or the compound according to formula (12) or (13), or mixture thereof, to obtain a desired diastereomeric purity for the C-5 stereogenic center; and e) isolating the compound according to formula (1), in such a way that the desired diastereomeric purity in compound of formula (1) is obtained, or by isolating any suitable salt thereof.

10. A method according to claim 1 or 9, wherein M is selected from the group consisting of Mg, Ce, Li, Ba, Al, B, Cu, Zn, Mn, Ti, Zr, and In.

11. A method according to claim 1 or 9, wherein each of M and M' of the formula $MM'(X)_n(Y)_{n'}$ is independently selected from the group consisting of Mg, Ce, Li, Ba, Al, B, Cu, Zn, Mn, Ti, Zr, and In.

12. A method according to claim 1 or 9, wherein $R_9$ is acetyl, trifluoroacetyl; $CF_3SO_2$, $CH_3SO_2$, $CH_3C_6H_4SO_2$, $C(O)OCH_3$, or $C(O)OC_4H_9$.

* * * * *